(12) United States Patent
Riedl et al.

(10) Patent No.: US 8,987,498 B2
(45) Date of Patent: Mar. 24, 2015

(54) ENANTIOMERICALLY PURE AMINES

(75) Inventors: Rosemarie Riedl, Vienna (AT); Werner Heilmayer, Zillingtal (AT); Lee Spence, Vienna (AT); Atchyuta Rama Chandra Murty Bulusu, Perchtoldsdorf (AT)

(73) Assignee: Nabriva Therapeutics AG, Vienna (AT)

( * ) Notice: Subject to any disclaimer, the term of this patent is extended or adjusted under 35 U.S.C. 154(b) by 0 days.

(21) Appl. No.: 13/699,585

(22) PCT Filed: May 23, 2011

(86) PCT No.: PCT/AT2011/000236
§ 371 (c)(1),
(2), (4) Date: Nov. 27, 2012

(87) PCT Pub. No.: WO2011/146953
PCT Pub. Date: Dec. 1, 2011

(65) Prior Publication Data
US 2013/0072711 A1    Mar. 21, 2013

(30) Foreign Application Priority Data
May 26, 2010  (EP) ................................... 10450093

(51) Int. Cl.
| | | |
|---|---|---|
| C07C 321/00 | (2006.01) | |
| C07C 271/24 | (2006.01) | |
| C07C 61/22 | (2006.01) | |
| C07C 211/40 | (2006.01) | |
| C07C 247/22 | (2006.01) | |
| C07C 265/10 | (2006.01) | |
| C07C 323/41 | (2006.01) | |
| C07C 323/43 | (2006.01) | |
| C07C 327/30 | (2006.01) | |
| C07D 303/36 | (2006.01) | |
| C07C 231/12 | (2006.01) | |
| C07C 231/14 | (2006.01) | |
| C07C 233/63 | (2006.01) | |
| C07C 269/04 | (2006.01) | |
| C07C 269/06 | (2006.01) | |

(52) U.S. Cl.
CPC .............. *C07C 271/24* (2013.01); *C07C 61/22* (2013.01); *C07C 211/40* (2013.01); *C07C 247/22* (2013.01); *C07C 265/10* (2013.01); *C07C 323/41* (2013.01); *C07C 323/43* (2013.01); *C07C 327/30* (2013.01); *C07D 303/36* (2013.01); *C07C 231/12* (2013.01); *C07C 231/14* (2013.01); *C07C 233/63* (2013.01); *C07C 269/04* (2013.01); *C07C 269/06* (2013.01); *C07C 2101/14* (2013.01); *C07C 2101/16* (2013.01)
USPC .......................................................... 560/9

(58) Field of Classification Search
USPC ..................... 560/9, 12, 13, 17; 564/123, 211
See application file for complete search history.

(56) References Cited

FOREIGN PATENT DOCUMENTS

| | | |
|---|---|---|
| WO | WO2008/113089 | 9/2008 |
| WO | WO 2008/113089 A1 * | 9/2008 |

OTHER PUBLICATIONS

Green et al. A-D743,(Protective groups in Organic Synthesis, Wiley-Interscience, New York, 1999, pp. 564-566 and 740-743.*
T. W. Greene, P. G. M. Wuts, *Protective Groups in Organic Synthesis*, Wiley-Interscience, 4th edition, 2007, particularly p. 696-868.
Pfister, J. R.; Wymann, W. E., Synthesis, 1983, 38-40.
International Search Report dated Jan. 12, 2011 in relation to PCT Application No. PCT/AT2011/000236.
Fletcher, S. R. et al., J. Chem. Soc., Chem. Commun. 1993, 59, 1216-1218.
E. Gómez-Sánchez et. Al: „Synthesis of 7-Azabicyclo[2.2.1]heptane and 2-Oxa-4-azabicyclo[3.3.1]non-3-ene Derivatives . . . , J. Org. Chem. 2007, 72, 8656-8670.
Gómez-Sánchez, E.; et. al., Tetrahedron 2005, 61, 1207-1219.
Legraverend, M.; Boumchita, H.; and Bisagni, E. J., Heterocyclic Chem., 1990, 27, 1801-1804.
A. Krief et al: "Diastereoselective Bromination of Compounds Bearing a Cyclohex-3-eno Moiety . . . ", J. Org. Chem. 2008, vol. 73, p. 9795-9797.
P. O'Brien et al: "cis- and trans-Stereoselective Epoxidation of N-protected 2-Cyclohexen-1-ylamines", Organic Letters, vol. 5, No. 26, 2003, p. 4955-1957.
Kapferer, P.; Vasella, A., Helvetica Chimica Acta 2004, 87, 2764-2789.

* cited by examiner

*Primary Examiner* — Yong Chu
*Assistant Examiner* — Blaine G Doletski
(74) *Attorney, Agent, or Firm* — Workman Nydegger

(57) ABSTRACT

A compound of formula

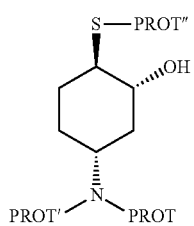

I wherein PROT is an amine protecting group and PROT' is hydrogen; or PROT and PROT' together with the nitrogen atom to which they are attached form a heterocyclic ring as an amine protecting group, and PROT" is a thiol protecting group, processes for its production, intermediates in their production and production of intermediates in stereoisomerically pure form, and their use for the production of pharmaceutically active compounds.

19 Claims, 2 Drawing Sheets

ENANTIOMERICALLY PURE AMINES

The present invention relates to enantiomerically pure amines, such as amino and thio protected hydroxy-mercapto-cyclohexyl amines and production processes thereof.

Organic compounds, such as cyclohexyl amines containing an asymmetric carbon atom may exist in the form of enantiomers, diastereoisomers and mixtures thereof, e.g. racemates. Such compounds may exist in the (R)—, (S)— or (R,S)-configuration. For pharmaceutical use it is often vital to have an active compound comprising an asymmetric carbon atom in one of the enantiomerically pure forms, since one isomer may differ, e.g. in several aspects from another isomer, e.g. one isomer may be more active than the other isomer. Separation of isomers is often burdensome. Chromatography which, for example, may be useful for isomeric separation, is on technical scale not easy to carry out and often needs sophisticated and expensive means.

Surprisingly it was now found that enantiomerically pure amino and thio protected hydroxy-mercapto-cycloalkyl amines with interesting pharmaceutical characteristics may be produced on technical scale. In the course of the production process according to the present invention interesting enantiomerically and regioisomerically pure compounds may be isolated, e.g. in solid, such as in crystalline form, from the reaction mixture.

Enantiomerically pure amino and thio protected hydroxy-mercapto-cyclohexyl amines according to the present invention were found to be important intermediates for the production of enantiomerically pure hydroxy-mercapto-cyclohexyl amines, which are attached to a pleuromutilin, e.g. which are attached via a thiomethylcarbonyl group to a mutilin, e.g. which are attached via a thiomethylcarbonyl group to the oxygen in position 14 of the mutilin ring. Pleuromutilins comprising such enantiomerically pure hydroxy-mercapto-cyclohexyl amines have been found to be pharmaceutically interesting, such as 14-O-{[4-amino-2-hydroxy-cyclohexyl)sulfanyl]-acetyl}-mutilins, as disclosed in WO2008/113089 which are described to be useful for treating microbial diseases.

In one aspect the present invention provides a compound of formula

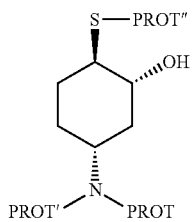

I wherein
PROT is an amine protecting group and PROT' is hydrogen; or
PROT and PROT' together with the nitrogen atom to which they are attached form a heterocyclic ring as an amine protecting group, and
PROT" is a thiol protecting group.

Amine protecting groups PROT and PROT' are known and may be obtained as appropriate, e.g. according to a method as conventional. Well known PROT groups include e.g. groups connected to the amine via an oxy- or carbonyloxy-, carbonyl- or oxycarbonyl-, $SO_2$—, arylalkyl, e.g. including triphenylmethyl, or C=N double bond.

Alternatively PROT and PROT' together with the nitrogen atom to which they are attached form a heterocyclic ring, e.g. the nitrogen atom together with PROT and PROT' to which they are attached is part of a phthalimido ring; removable, e.g. by treatment with hydrazine.

Groups PROT or PROT', respectively, are removable under acidic, basic, hydrogenating, oxidative or reductive conditions, e.g. by hydrogenolysis, treatment with an acid, a base, a hydride, a sulfide.

For example, PROT' is hydrogen, and PROT is, e.g. selected from
- benzyloxycarbonyl (Cbz), removable e.g. by hydrogenolysis,
- p-methoxybenzylcarbonyl (Moz or MeOZ), removable e.g. by hydrogenolysis,
- tert-butyloxycarbonyl (BOC), removable e.g. by treatment with a strong acid, such as HCl, $H_3PO_4$, or $CF_3COOH$,
- 9-fluorenylmethyloxycarbonyl (FMOC), removable e.g. by treatment with a base, such as piperidine,
- trifluoroacetyl, removable e.g. by treatment with base, such as NaOH, $K_2CO_3$
- benzyl (Bn), removable e.g. by hydrogenolysis;
- p-methoxybenzyl (PMB), removable e.g. by hydrogenolysis;
- 3,4-dimethoxybenzyl (DMPM), removable e.g. by hydrogenolysis;
- p-methoxyphenyl (PMP), removable e.g. by treatment with ammonium cerium (IV) nitrate (CAN),
- tosyl (Tos), removable e.g. by treatment with concentrated acid, such as HBr, $H_2SO_4$, or by treatment with strong reducing agents, such as sodium in liquid ammonia, sodium naphthalene,
- groups which form with the amine sulfonamides other than Tos-amides, e.g. including 2-nitrobenzenesulfonamide (nosyl) or o-nitrophenylsulfenyl (Nps), removable e.g. by treatment with samarium iodide, tributyltin hydride,
- benzylidene, removable e.g. by treatment with trifluoromethanesulfonic acid, $CF_3COOH$, dimethyl sulfide;
- triphenylmethyl (trityl, Tr), dimethoxytrityl (DMT), e.g. removable by treatment with an acid, such as $CF_3COOH$.

In a compound of formula I, preferably PROT is an amine protecting group and PROT' is hydrogen.

In a compound of formula I, more preferably PROT is tert-butoxycarbonyl (BOC) or ethoxycarbonyl or trifluoroacetyl and PROT' is hydrogen, most preferably PROT is trifluoroacetyl and PROT' is hydrogen.

In a further aspect in a compound of formula I a group PROT includes a group of formula —CO—R, wherein R together with CO to which it is attached is an amine protecting group, e.g. a electron withdrawing group, e.g. a leaving group, such as ($C_{1-8}$)alkoxy, e.g. tert-butoxy or ethoxy; or ($C_{1-8}X_{1-17}$)alkyl, wherein X is halogen, such as trihaloalkyl, e.g. $CF_3$; or $C_{6-12}$aryl, e.g. phenyl, e.g. including phenyl-carbonyloxy-methyl-phenyl, e.g. of formula

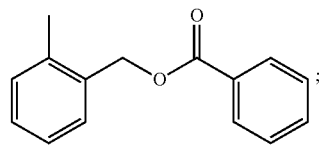 [SMILES: Cc1ccccc1COC(=O)c1ccccc1];

preferably in one aspect R is tert-butoxy, ethoxy or CF$_3$ and PROT' preferably is hydrogen, most preferably R is CF$_3$ and PROT' is hydrogen.

Appropriate amine protecting groups e.g. are described in T. W. Greene, P. G. M. Wuts, *Protective Groups in Organic Synthesis*, Wiley-Interscience, 4$^{th}$ Edition, 2007, particularly p. 696-868.

PROT" is a thiol protecting group, e.g. including
- (C$_{1-6}$)alkyl, wherein alkyl optionally is further substituted, e.g. further substituted by (C$_{6-12}$)aryl e.g. phenyl, such as trityl; e.g. removable by strong acid or AgNO$_3$
- (C$_{1-6}$)alkylcarbonyl, e.g. acetyl, e.g. removable by base, such as sodium oxide treatment
- (C$_{6-12}$)arylcarbonyl, e.g. benzoyl, e.g. removable by treatment with reduction agent, such as DIBAL, or treatment with a base, such as hydrazine In a compound of formula I preferably PROT" is benzoyl or trityl, most preferably PROT" is benzoyl.

Appropriate sulfur protecting groups e.g. are described in T. W. Greene, P. G. M. Wuts, *Protective Groups in Organic Synthesis*, Wiley-Interscience, 4$^{th}$ Edition, 2007, particularly p. 647-695.

A compound of formula I comprises a compound of formula $I_S$

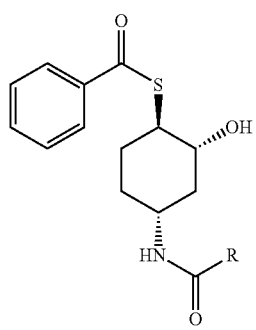

wherein PROT is as defined above; and in another aspect the present invention provides a compound of formula $I_S$, wherein PROT is an amine protecting group.

A compound of formula $I_S$ comprises a compound of formula $I_{SS}$

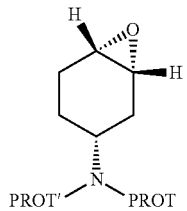

wherein R is as defined above; and in a further aspect the present invention provides a compound of formula $I_{SS}$, wherein R is as defined above.

A compound of formula $I_{SS}$ comprises a compound of formula $I_{SSS}$

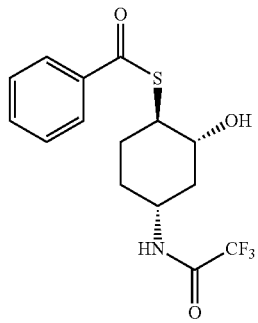

and in a further aspect the present invention provides a compound of formula $I_{SSS}$.

Surprisingly, according to the present invention certain compounds useful in a process according to the present invention were found in crystalline form.

In another aspect the present invention provides {(1R,2R,4R)-4-[(tert-butoxycarbonyl)-amino]-2-hydroxy-cyclohexyl}-benzene-carbothioate, in crystalline form, e.g. which is characterized by an X-ray powder diffraction pattern with peaks 2-theta at (degrees, ±0.2, inter alia):
6.3, 12.7, 16.6, 17.9, 21.2; such as:
6.3, 12.7, 14.1, 16.6, 17.9, 21.2, 23.0, 24.7.

In another aspect the present invention provides {(1R,2R,4R)-4-[(2,2,2-trifluoro-acetyl)-amino]-2-hydroxy-cyclohexyl}-benzene-carbothioate, in crystalline form, e.g. which is characterized by an X-ray powder diffraction pattern with peaks 2-theta at (degrees, ±0.2, inter alia):
6.7, 13.3, 19.7, 20.0, 20.8, 26.8, 39.0; such as:
6.7, 10.9, 13.3, 19.7, 20.0, 20.8, 24.4, 26.8, 28.8, 39.0.

A compound of formula I may be obtained by oxiran ring opening under introduction of a sulfur group in the side chain of the cyclohexyl ring in a compound of formula

II

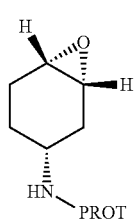

wherein PROT and PROT' are as defined above; e.g. by reaction with an optionally activated PROT"-thiol, wherein PROT" is defined as above.

Analogously as a compound of formula I, a compound of formula $I_S$ may be obtained by oxiran ring opening under introduction of a sulfur group in the side chain of the cyclohexyl ring in a compound of formula $II_S$ wherein PROT is as defined above.

Analogously as a compound of formula I, a compound of formula $I_{SS}$ may be obtained by oxiran ring opening under introduction of a sulfur group in the side chain of the cyclohexyl ring in a compound of formula

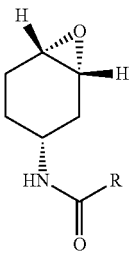

$II_{SS}$ wherein R is as defined above.

Analogously as a compound of formula I, a compound of formula $I_{SSS}$ may be obtained by oxiran ring opening under introduction of a sulfur group in the side chain of the cyclohexyl ring in a compound of formula

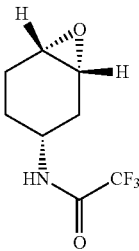

$II_{SSS}$

Oxiran ring opening under introduction of a sulfur group in the side chain of the cyclohexyl ring in any of the compounds II, $II_S$, $II_{SS}$ or $II_{SSS}$, respectively, per se is a known reaction and may be performed as appropriate, e.g. according, e.g. analogously to a method as conventional, or as described herein. In one embodiment of the present invention ring opening is carried out by reacting a compound of formula II, $II_S$, $II_{SS}$ or $II_{SSS}$, respectively, with a sulfur donating group, optionally in the presence of an activating agent, such as tetrabutylammonium chloride or a base, such as 1,5-diazabicyclo[4.3.0]non-5-ene (DBN) or 1,8-diazabicyclo[5.4.0]undec-7-ene (DBU), in a solvent, e.g. organic solvent such as halogenated hydrocarbon, e.g. chlorobenzene, aromatic hydrocarbon, e.g. toluene or a nitrile, e.g. acetonitrile.

A sulfur donating group which is useful in a process for oxiran ring opening according to the present invention includes e.g.
- a $(C_{1-6})$alkyl-thiol, wherein alkyl optionally is further substituted, e.g. further substituted by $(C_{6-12})$aryl such as phenyl, such as a trityl-thiol;
- a $(C_{1-6})$alkyl-thio acid, e.g. thioacetic acid,
- a $(C_{6-12})$aryl-thio acid, e.g. thiobenzoic acid;

preferably thiobenzoic acid or trityl-thiol, most preferably thiobenzoic acid.

According to the present invention it was found that compounds of formula I, $I_S$, $I_{SS}$ or $I_{SSS}$ respectively, may be obtained separated from the respective regioisomer of formula IR, $IR_S$, $IR_{SS}$ or $IR_{SSS}$, respectively

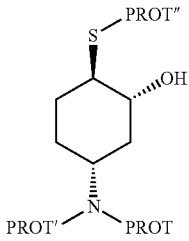

I

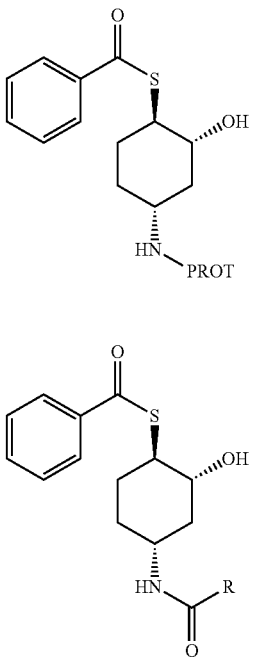

$I_S$ $I_{SS}$ $I_{SSS}$

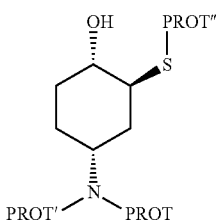

IR

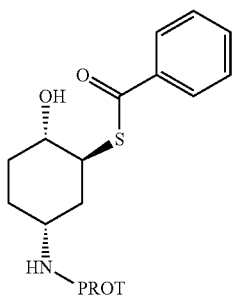

$IR_S$

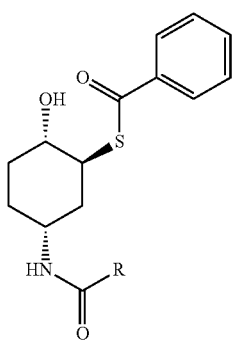

$IR_{SS}$

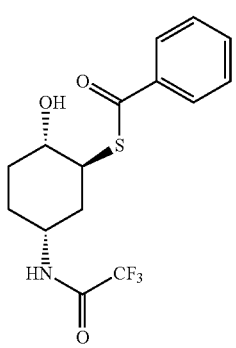

$IR_{SSS}$ wherein PROT and PROT', PROT" and R are as defined above, in high yield and high chemical purity.

Separation of the racemic mixtures of regioisomers is described in WO2008/113089, e.g. in example 34 (separation of a compound of formula $I_S$ plus its enantiomer from the mixture of a compound of formula $I_S$ plus its enantiomer and a compound of formula $IR_S$ plus its enantiomer, wherein PROT is BOC) for the racemic mixture via precipitation in low yield.

According to the present invention its was surprisingly found that with optimization of the process conditions, e.g. volumes and/or equivalents, the yield of a compound of formula $I_S$, wherein PROT is BOC, is significantly enhanced compared to the procedure described in WO2008/113089. In the following TABLE 1 the enhancement of yield obtained via crystallization according to the present invention compared to the process described in WO2008/113089 is indicated.

TABLE 1

|  | WO2008/113089 | Present Invention |
|---|---|---|
| Product | {(1R,2R,4R)-4-[(tert-Butoxycarbonyl)-amino]-2- | {(1R,2R,4R)-4-[(tert-Butoxycarbonyl)-amino]-2- |

TABLE 1-continued

|  | WO2008/113089 | Present Invention |
|---|---|---|
|  | hydroxy-cyclohexyl}-benzene-carbothioate and {(1S,2S,4S)-4-[(tert-Butoxycarbonyl)-amino]-2-hydroxy-cyclohexyl}-benzene-carbothioate | hydroxy-cyclohexyl}-benzene-carbothioate |
| Yield | 21% | ≥30% |

Furthermore, according to the present invention the achieved chemical purity is surprisingly high, e.g. ≥95, even. ≥97%.

Separation of the regioisomers may be carried out via crystallization from a solvent, such as an organic solvent, e.g. an aromatic solvent, such as toluene or chlorobenzene, optionally via addition of an antisolvent, such as an apolar organic solvent, e.g. an aliphatic hydrocarbon, such as heptane and treating the crystalline solid obtained with a solvent mixture, e.g. a mixture of an aromatic solvent with an aliphatic hydrocarbon, such as a toluene/heptane mixture or a chlorobenzene/heptane mixture to obtain a compound of formula I, $I_S$, $I_{SS}$, or $I_{SSS}$, respectively, separated from the undesired regioisomer IR, $IR_S$, $IR_{SS}$ or $IR_{SSS}$, respectively. The surprising straightforwardness and simplicity of this separation to obtain a compound of formula I, $I_S$, $I_{SS}$, or $I_{SSS}$, in high yield and purity is of particular relevance for the production on an industrial scale and avoids cumbersome and expensive separation procedures e.g. separation via chromatography The separation of regioisomers and isolation of a compound of formula $I_S$ or $I_{SS}$ wherein PROT is 2,2,2-trifluoro-acetyl or R is $CF_3$, respectively, (compound if formula $I_{SSS}$) is surprisingly even much more straightforward than the separation of regioisomers and isolation of a compound of formula $I_S$ or $I_{SS}$ wherein PROT is tert-butoxycarbonyl (BOC) or R is tert-butoxy, respectively.

According to the present invention surprisingly a significant enhancement of regioselectivity and thus a significantly higher yield of the desired regioisomer was found in the process for the production of a compound of formula $I_S$ or $I_{SS}$, wherein PROT is 2,2,2-trifluoro-acetyl or R is $CF_3$, respectively, (compound of formula $I_{SSS}$) compared to the process for the production of a compound of formula $I_S$ or $I_{SS}$, wherein PROT is tert-butoxycarbonyl (BOC) or R is tert-butoxy, respectively. In the following TABLE 2 the enhancement of regioselectivity in the epoxide ring opening reaction leading to an significantly higher overall yield for compounds of formula $I_S$ or $I_{SS}$ wherein PROT is 2,2,2-trifluoro-acetyl or R is $CF_3$, respectively, (compound of formula $I_{SSS}$) is indicated:

TABLE 2

| $I_S$ | PROT = tert-Butoxycarbonyl (BOC) | PROT = Trifluoroacetyl |
|---|---|---|
| $I_{SS}$ Regioselectivity in the Epoxide Ring-Opening Reaction I, $I_S$, $I_{SS}$:IR, $IR_S$, $IR_{SS}$ | R = tert-Butoxy ca. 1:1 | R = Trifluoromethyl ca. 3.5:1 |

Even more surprisingly the stability of a compound of formula $I_S$ or $I_{SS}$ wherein PROT is 2,2,2-trifluoro-acetyl or R is $CF_3$, respectively, (compound of formula $I_{SSS}$) is improved compared with that of a compound of formula $I_S$ or $I_{SS}$ wherein PROT is tert-butoxycarbonyl (BOC) or R is tert-butoxy, respectively. In the following TABLE 3 the enhancement of stability is exemplified with data for a storage temperature of 40° C. and 60° C. derived from individual batches:

TABLE 3

HPLC Data [% area]

| | $I_S$ | | | | |
|---|---|---|---|---|---|
| | PROT = tert-Butoxycarbonyl (BOC) | | PROT = Trifluoroacetyl | | |
| | $I_{SS}$ | | | | |
| | R = tert-Butoxy | | R = Trifluoromethyl | | |
| | Time | | | | |
| Temperature | 0 | 1 Week | 3 Months | 0 | 1 Week | 3 Months |
| 40° C. | 93.68 | — | 79.47 | 99.37 | — | 99.52* |
| 60° C. | 96.77 | 95.00 | — | 99.62 | 99.67* | — |

*The slightly higher area % values are within the HPLC method variation

As can be clearly seen from table 3 above the trifluoroacetyl protected compound is more stable upon storage than the compound protected with tert-butoxycarbonyl.

In a further aspect the present invention provides a compound of formula II, $II_S$, $II_{SS}$ or $II_{SSS}$ wherein PROT, PROT' and R are as defined above, preferably selected from the group consisting of tert-butyl (1R,3R,6R)-(7-oxa-bicyclo[4.1.0]hept-3-yl)-carbamate, and 2,2,2-trifluoro-N-(1R,3R,6S)-(7-oxa-bicyclo[4.1.0]hept-3-yl)-acetamide, and more preferably is trifluoro-N-(1R,3R,6S)-(7-oxa-bicyclo[4.1.0]hept-3-yl)-acetamide.

A compound of formula II, $II_S$, $II_{SS}$ or $II_{SSS}$, respectively may be obtained by epoxidation of the double bond in a compound of formula

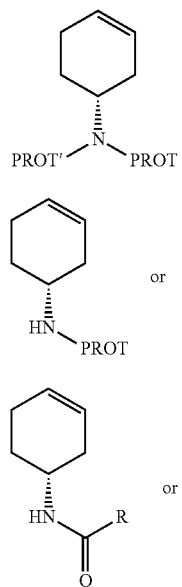

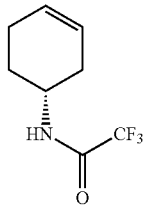

respectively, wherein PROT and PROT' and R are as defined above, and isolating a compound formula II, $II_S$, $II_{SS}$ or $II_{SSS}$, wherein PROT, PROT' and R are as defined above, obtained from the reaction mixture.

Epoxidation per se is a known process and may be carried out as appropriate, e.g. according, e.g. analogously to a method as conventional, or as described herein, e.g. by use of an oxidation agent, such as peracid, e.g. 3-chloroperbenzoic acid or peracetic acid in a solvent, e.g. organic solvent, such as $CH_2Cl_2$, chlorobenzene or toluene.

It was found, that the epoxidation works in favor of the syn (cis) compounds—as expected and as described in literature e.g. for a compound of formula II, $II_S$ wherein PROT is ethoxycarbonyl and PROT' is hydrogen; or PROT is 2,2,2-trifluoro-acetyl and PROT' is benzyl, respectively (e.g. Gómez-Sánchez, E.; Marco-Contelles, J. Tetrahedron 2005, 61, 1207-1219, Fletcher, S. R.; et al. J. Org. Chem., 1994, 59, 1771-1778).

However, it was also found in the literature that epoxidation works in favor of the anti (trans) compounds e.g. for a compound of formula II, $II_S$ wherein PROT is 2,2,2-trifluoroacetyl and PROT' is benzyl, respectively (e.g. Fletcher, S. R.; et al. J. Chem. Soc., Chem. Commun 1993, 59, 1216-1218).

According to the present invention surprisingly a significant enhancement for the desired syn (cis) selectivity in the epoxidation of compound of formula $III_S$ or $III_{SS}$, respectively wherein PROT is 2,2,2-trifluoro-acetyl or R is $CF_3$, respectively (compound of formula $III_{SSS}$) and thus a higher yield of a compound of formula $II_S$, $II_{SS}$, respectively wherein PROT is 2,2,2-trifluoro-acetyl or R is $CF_3$, respectively, (compound of formula $III_{SSS}$) was found compared with the selectivity in case of a compound of formula $III_S$ or $III_{SS}$, respectively wherein PROT is tert-butoxycarbonyl, or R is tert-butoxy, respectively which is shown in the following TABLE 4:

TABLE 4

| $II_S$ | PROT = tert-Butoxycarbonyl (BOC) | PROT = Trifluoroacetyl |
|---|---|---|
| $II_{SS}$ | R = tert-Butoxy | R = Trifluoromethyl |
| Syn/Anti-Selectivity in the Epoxidation Syn epoxide:anti epoxide | 3 to 4:1 | ca. 9:1 |

In another aspect the present invention provides a process for the production of a compound of formula II, $II_S$, $II_{SS}$ or $II_{SSS}$, respectively, wherein PROT, PROT' and R are as defined above, comprising epoxidizing the double bond in a compound of formula III, $III_S$, $III_{SS}$ or $III_{SSS}$, respectively, wherein PROT and PROT' and R are as defined above, and isolating a compound of formula II, $II_S$, $II_{SS}$ or $II_{SSS}$, respectively, obtained from the reaction mixture.

Compounds of formula III, $III_S$ or $III_{SS}$ may be obtained as appropriate, e.g. according, e.g. analogously, to a method as conventional or as described herein, e.g. by protecting the amine group in a compound of formula

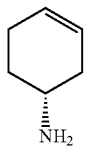

IV respectively, optionally in salt form, e.g. in the form of a hydrochloride,
either with an amine protecting group PROT-L or

wherein L is an electron withdrawing group, e.g. a leaving group,
or by acylation or carbamoylation,
  e.g. by reaction with a an activated carboxylic acid or carboxylic acid derivative, such as an anhydride of a carboxylic acid, or carboxylic acid halogenide;
  e.g. by reaction with an activated carboxylic acid or carboxylic acid derivative, wherein an electron withdrawing group is present, e.g. a leaving group, such as a compound of formula L-CO-R, wherein R and L are as defined above,
  e.g. by reaction with an activated trihaloalkyl or $C_{6-12}$aryl carboxylic acid, or with an activated carboxylic acid $(C_{1-6})$alkyl ester, to obtain a compound of formula III, $III_S$, $III_{SS}$ or $III_{SSS}$ respectively.

Compounds of formula III, $III_S$, $III_{SS}$ or $III_{SSS}$ may also be obtained by a Curtius rearrangement from a compound of formula

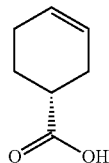

V by treating a compound of formula V with an azidoylation agent, namely an agent which is able to form an azidocarbonyl group from a carboxyl group, such as diphenylphosphoryl azide (DPPA), in the presence of a base, e.g. an amine, such as $(C_2H_5)_3N$, to form the azido carbonyl of formula

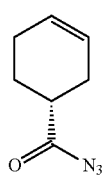

VI respectively, which under loss of nitrogen, rearranges to an isocyanate of formula

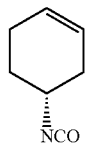

VII by treatment in organic solvent, such as halogenated hydrocarbon, e.g. $CH_2Cl_2$, chlorobenzene or toluene, and treating the isocyanate obtained with an alcohol, such as a $(C_{1-8})$alkylalcohol, e.g. a $(C_{1-6})$alkylalcohol, such as tert-butanol, optionally in the presence of CuCl (Kapferer, P.; Vasella, A. Helvetica Chimica Acta 2004, 87, 2764-2789), to obtain a compound of formula III or $III_S$, respectively, wherein PROT is —CO—$C_{1-8}$alkoxy, e.g. including —CO—$C_{1-6}$alkoxy, e.g. tert-butoxycarbonyl (BOC); or to obtain a compound of formula $III_{SS}$, wherein R is $C_{1-8}$alkoxy, e.g. including $C_{1-6}$alkoxy, such as tert-butoxy; or treating the isocyanate obtained with a strong organic acid, such as $(C_{1-8}X_{1-17})$alkylCOOH, wherein X is halogen, such as a trihalogenacetic acid, e.g. including $CF_3COOH$ (Pfister, J. R.; Wymann, W. E. Synthesis, 1983, 38-40), optionally in the presence of CuCl, to obtain a compound of formula III or $III_S$, respectively, wherein PROT is —CO—$(C_{1-8}X_{1-17})$alkyl, e.g. including —CO—$CX_3$, wherein X is halogen, e.g. trifluoroacetyl (compound of formula $III_{SSS}$); or to obtain a compound of formula $III_{SS}$ wherein R is $(C_{1-8}X_{1-17})$alkyl, wherein X is halogen, such as trihalogenmethyl, e.g. including trifluoromethyl.

In the Curtis rearrangement process provided according to the present invention compounds of formula VI or VII are preferably not isolated.

A compound of formula V may be obtained from a compound of formula

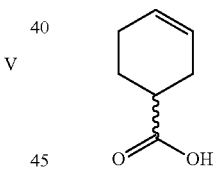

VIII by enantiomeric separation e.g. via diastereomeric salts.

Separation of enantiomers of 3-cyclohexene carboxylic acid of formula VIII may be carried out by reaction with a chirally pure amine, e.g. reaction with (R)-(+)-α-methylbenzylamine to obtain 3-cyclohexene-1S-carboxylic acid, or with (S)-(−)-α-methylbenzylamine to obtain 3-cyclohexene-1R-carboxylic acid. The salt product obtained in such separation may be subjected to one or more recrystallizations until a required optical rotation ($^{20}[α]_D$>+40° for 3-cyclohexene-1R-carboxylic acid (S)-(−)-α-methylbenzylamine salt and $^{20}[α]_D$>−40° for 3-cyclohexene-1S-carboxylic acid (R)-(+)-α-methylbenzylamine salt) is achieved. The carboxylic acid of formula V may be provided by salt release under acidic conditions. A compound of formula V, cyclohex-3-ene-1(R)-carboxylic acid, may be obtained in analogy to the method disclosed in Schwartz, H. M.; et al. JACS 1978, 100, 5199-5203.

A compound of formula III, $III_S$, $III_{SS}$ or $III_{SSS}$ in a pure stereoisomeric form may also be obtained from a carboxylic acid of formula V by reaction with an acid halogenide, e.g.

acid chloride forming agent, e.g. (COCl)$_2$ to obtain the carboxylic acid chloride of formula

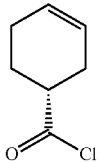

IX

The acid chloride obtained may be further reacted with NaN$_3$ to obtain the corresponding acyl azide of formula V.

The acyl azide of formula V obtained may be subjected to a Curtius rearrangement to obtain the corresponding isocyanate of formula VII. The isocyanate of formula VII obtained may be hydrolyzed, e.g. in the presence of an aqueous acid, e.g. HCl, to obtain a corresponding free amine, optionally in the form of a salt, such as an acid addition salt, e.g. a hydrochloride of formula IV or addition to the isocyanate may be carried out in the presence of an alcohol and optionally CuCl, to obtain a carboxylated amine of formula III, III$_S$ or III$_{SS}$, respectively; e.g. if tert-butyl alcohol is present as an alcohol the tert-butoxycarbonyl protected amine is obtained, e.g. if ethanol is present as an alcohol, the ethoxycarbonyl protected amine is obtained, in which amine or carboxylated amine is an amine or carboxylated amine according to the present invention of formula III$_S$, wherein PROT is tert-butoxycarbonyl or ethoxycarbonyl; or of formula III$_{SS}$, wherein R is tert-butoxy or ethyloxy; or the isocyanate of formula VII obtained may be reacted with an strong organic acid, such as (C$_{1-8}$X$_{1-17}$)alkylCOOH wherein X is halogen, such as a trihalogenacetic acid, e.g. including CF$_3$COOH, optionally in the presence of CuCl, to obtain a carboxylated amine of formula III$_S$ or III$_{SS}$, respectively; e.g. if CF$_3$COOH is used as strong organic acid, the trifluoroacetyl protected amine is obtained, in which amine or carboxylated amine is an amine or carboxylated amine according to the present invention of formula III$_S$, wherein PROT is trifluoroacetyl; or of formula III$_{SS}$ wherein R is trifluoromethyl (compound of formula III$_{SSS}$).

Compounds of formula III, III$_S$, III$_{SS}$, III$_{SSS}$, IV, V, VI, VII and IX in their racemic form (in a mixture with their respective enantiomers) are described the literature (e.g. Kapferer, P.; Vasella, A. Helvetica Chimica Acta 2004, 87, 2764-2789; Pfister, J. R.; Wymann, W. E. Synthesis, 1983, 38-40; Gómez-Sánchez, E.; et. al. J. Org. Chem. 2007, 72, 8656-8670; Gómez-Sánchez, E.; et. al. Tetrahedron 2005, 61, 1207-1219; Legraverend, M.; Boumchita, H.; and Bisagni, E. J. Heterocyclic Chem., 1990, 27, 1801-1804).

In another aspect the present invention provides a process for the preparation of a compound of formula I, I$_S$, I$_{SS}$ or I$_{SSS}$, respectively, wherein PROT, PROT' and R as defined above and PROT' is hydrogen comprising a) either reacting a compound of formula V with an azidoyl forming agent, optionally diphenylphosphoryl azide, such as diphenylphosphoryl azide, optionally in the presence of a base,
or reacting compound of formula V with an acid chloride forming agent, optionally oxalyl chloride or thionyl chloride, such as oxalylchloride, to obtain a compound of formula IX, and further reacting a compound of formula IX with sodium azide,
to obtain the acyl azide of formula VI, b) subjecting the acyl azide of formula VI, e.g. obtained in step a), to a Curtius rearrangement to obtain an isocyanate of formula VII,
c) either reacting the isocyanate of step b) either via addition of an alcohol or reaction with a strong organic acid and optionally in the presence of CuCl,
or subjecting a compound of formula VII to hydrolysis with subsequent loss of carbon dioxide to obtain a compound of formula IV, which compound of formula IV is protected with an amino protecting group, optionally in the presence of base,
to obtain a compound of formula III, III$_S$, III$_{SS}$ or III$_{SSS}$, respectively, wherein PROT and R are as defined above and PROT' is hydrogen,
d) subjecting a compound of formula III, III$_S$, III$_{SS}$ or III$_{SSS}$, respectively, e.g. obtained in step c), to epoxidation by use of an oxidation agent to obtain a corresponding oxiran of formula II, II$_S$, II$_{SS}$ or II$_{SSS}$, respectively, wherein PROT, PROT' and R are as defined above and PROT' is hydrogen,
e) subjecting a compound of step d) to oxiran ring opening under introduction of a sulfur group in the side chain of the cyclohexyl ring via a sulfur donating agent, and
f) direct isolating a compound of formula I, I$_S$, I$_{SS}$ or I$_{SSS}$, wherein PROT, PROT' and R are as defined above, and PROT' is hydrogen,
optionally by addition of an appropriate anti solvent,
optionally whereby the reaction a) to e) is performed in a single solvent (system), and/or whereby none of the intermediates obtained in a) to d) is isolated,
and isolating a compound of formula I, I$_S$, I$_{SS}$ or I$_{SSS}$ in the form of a crystalline solid, from the reaction mixture.

In the above process preferably the reaction a) to e) is performed in a single solvent (system), such as toluene or chlorobenzene, if a compound of formula III, III$_S$, III$_{SS}$ or III$_{SSS}$ is prepared from a compound of formula V via an azidoyl forming agent to obtain a compound of formula VI; and after Curtius rearrangement obtaining the isocyanate of formula VII which is further reacted with a strong acid or alcohol.

In the above process, if a compound of formula III, III$_S$, III$_{SS}$ or III$_{SSS}$ is prepared from a compound of formula V via an azidoyl forming agent, preferably none of the intermediates obtained in a) to d) is isolated, e.g. the product obtained in a) to d), respectively, is directly further reacted in solution and only a compound obtained in e), namely a compound of formula I, I$_S$, I$_{SS}$ or I$_{SSS}$ is isolated, e.g. in the form of a crystalline solid, from the reaction mixture.

The above processes starting from a compound of formula V, may provide a compound of formula I, I$_S$, I$_{SS}$ or I$_{SSS}$, respectively, starting from a compound of formula V, without the necessity to use any chromatography and is therefore particularly useful in large scale manufacturing. In addition, the use of a single solvent (system) starting from a compound of formula V to obtain the desired compounds of formula I, I$_S$, I$_{SS}$ or I$_{SSS}$, respectively, make the above processes extremely useful and minimizes the waste of chemicals i.e. solvents. All the described processes including the processes of the present invention are highly compatible for large scale manufacture.
Compounds of Formula
I, I$_S$, I$_{SS}$ or I$_{SSS}$ (also designated herein as compound(s) of formula I");
II, II$_S$, II$_{SS}$ or II$_{SSS}$ (also designated herein as compound(s) of formula II");
III, III$_S$, III$_{SS}$ or III$_{SSS}$ (also designated herein as compound(s) of formula III"); IV, V, VI, VII or IX
are in stereoisomerically pure form as indicated in the formula drawings herein.

"Stereoisomerically pure form" as indicated in the drawings herein designates a form wherein the compound shows a diastereomeric or enantiomeric excess of ≥90% of the indicated stereochemistry.

Compounds of formula II", III", IV, V, VI, VII or IX, wherein the residues are as defined above, all are provided in a stereoisomerically pure form and are useful for the production of a compound of formula I" in a stereoisomerically pure form.

In another aspect the present invention provides the use of a compound of formula II", III", IV, V, VI, VII or IX for the production of a compound of formula I".

Compounds of formula I" are useful for the production of pharmaceutically active compounds, e.g. as disclosed in WO2008/113089.

A compound of formula I" may be obtained from a compound of formula II", III", IV, V, VI, VII or IX, respectively as an intermediate without chromatography which constitutes an enormous advantage, e.g. particularly in a production process on technical scale.

Preferred compounds of the present invention include compounds selected from the group consisting of
tert-Butyl (1R,3R,6R)-(7-oxa-bicyclo[4.1.0]hept-3-yl)-carbamate,
{(1R,2R,4R)-4-[(tert-Butoxycarbonyl)-amino]-2-hydroxy-cyclohexyl}-benzene-carbothioate,
2,2,2-Trifluoro-N-(1R,3R,6S)-(7-oxa-bicyclo[4.1.0]hept-3-yl)-acetamide,
{(1R,2R,4R)-4-[(2,2,2-Trifluoro-acetyl)-amino]-2-hydroxy-cyclohexyl}-benzene-carbothioate,
tert-Butyl [(1R,3R,4R)-3-hydroxy-4-tritylsulfanyl-cyclohexyl]-carbamate, and
2,2,2-Trifluoro-N-((1R,3R,4R)-3-hydroxy-4-tritylsulfanyl-cyclohexyl)-acetamide.

Particularly preferred compounds of the present invention include compounds selected from the group consisting of
tert-Butyl (1R,3R,6R)-(7-oxa-bicyclo[4.1.0]hept-3-yl)-carbamate,
{(1R,2R,4R)-4-[(tert-Butoxycarbonyl)-amino]-2-hydroxy-cyclohexyl}-benzene-carbothioate,
2,2,2-Trifluoro-N-(1R,3R,6S)-(7-oxa-bicyclo[4.1.0]hept-3-yl)-acetamide, and
{(1R,2R,4R)-4-[(2,2,2-Trifluoro-acetyl)-amino]-2-hydroxy-cyclohexyl}-benzene-carbothioate.

Most preferred compounds of the present invention include compounds selected from the group consisting of
2,2,2-Trifluoro-N-(1R,3R,6S)-(7-oxa-bicyclo[4.1.0]hept-3-yl)-acetamide, and
{(1R,2R,4R)-4-[(2,2,2-Trifluoro-acetyl)-amino]-2-hydroxy-cyclohexyl}-benzene-carbothioate.

Any compound provided by the present invention is also designated herein as "a compound(s) of (according to) the present invention" and any process provided by the present invention is designated herein as "a process(es) of (according to) the present invention".

Figure 1:
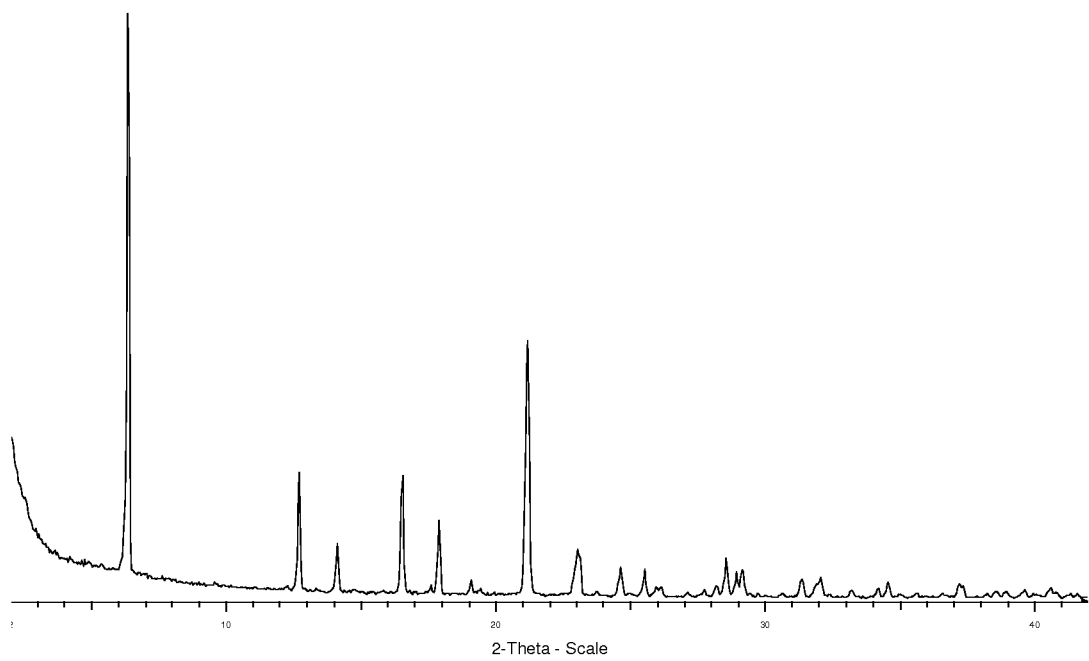
In FIG. 1 the Powder Diffractogram of {(1R,2R,4R)-4-[(tert-Butoxycarbonyl)-amino]-2-hydroxy-cyclohexyl}-benzene-carbothioate is indicated.
Figure 2:
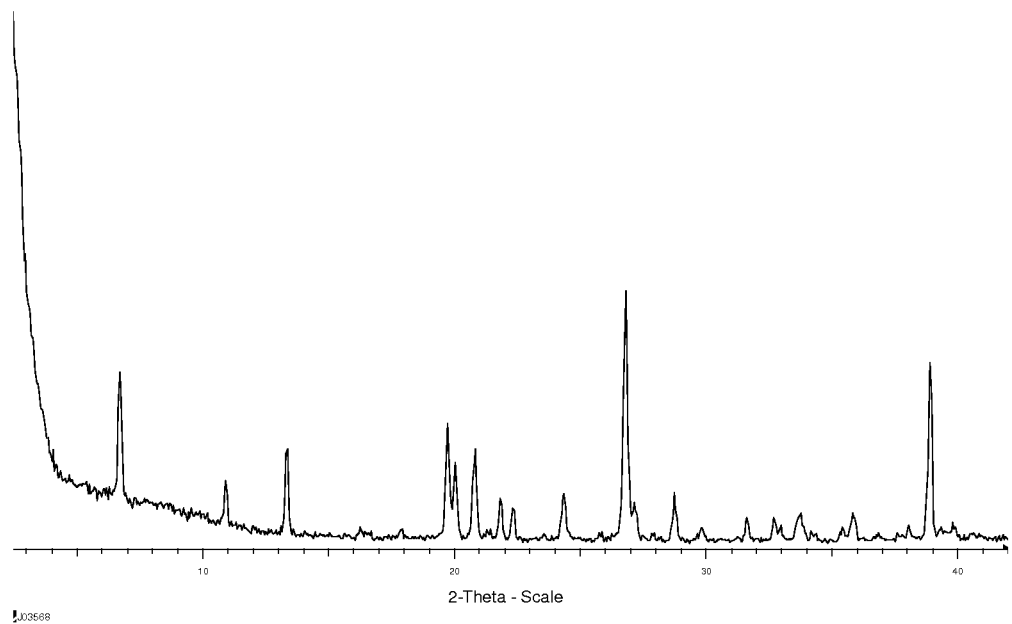
FIG. 2 shows the Powder Diffractogram of {(1R,2R,4R)-4-[(2,2,2-Trifluoro-acetyl)-amino]-2-hydroxy-cyclohexyl}-benzene-carbothioate.

In the following examples all temperatures are in ° C. and are uncorrected.

The following abbreviations are used:
° C. degrees Celsius
$^1$H NMR proton nuclear magnetic resonance spectroscopy
$^{13}$C NMR carbon nuclear magnetic resonance spectroscopy
$[\alpha]_D$ specific optical rotation angle at 589 nm
c concentration in g/100 ml
DBN 1,5-diazabicyclo[4.3.0]non-5-ene
DBU 1,8-diazabicyclo[5.4.0]undec-7-ene
DMF N,N-dimethylformamide
DMSO dimethylsulfoxide
DPPA diphenyl phosphoryl azide
ESI electrospray ionization
Et ethyl
EtOAc ethyl acetate
h hour(s)
heptane n-heptane
HPLC high performance liquid chromatography
KF Karl Fischer
min minute(s)
mCBA 3-chlorobenzoic acid
mCPBA 3-chloroperbenzoic acid
M molarity
MeOH methanol
mp melting point
MS mass spectrometry
MTBE methyl tert-butyl ether
m/z mass/charge ratio
rt room temperature
TLC thin layer chromatography
wt weight A "strip weight assay" as indicated in the examples is defined as follows: The content of an aliquot of a batch or of the whole batch is determined by removing the solvent and determining the content by HPLC or NMR using an internal or external standard and/or subtracting known impurities from the compound. In case of taking an aliquot a back extrapolation to the total mass/volume is performed.

A "line rinse" as indicated in the examples is a system rinse using an appropriate solvent to minimize losses of product and input materials.

EXAMPLE 1

{(1R,2R,4R)-4-[(tert-Butoxycarbonyl)-amino]-2-hydroxy-cyclohexyl}-benzene-carbothioate Step A. Salt Formation of cyclohex-3-ene-1-carboxylic acid

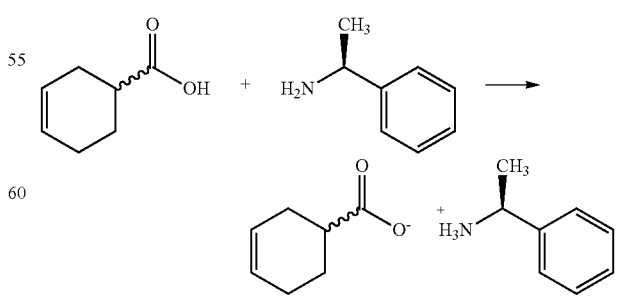

1000 g of racemic cyclohex-3-ene-1-carboxylic acid was charged to a flask and 5 volumes of acetone were added. The mixture obtained was stirred, heated to 55 to 60° C. and stirred for 30 min. To the mixture obtained 960.5 g of (S)-(−)-α-methylbenzylamine in 2 volumes of acetone was added dropwise over approximately 25 min. A clear orange solution was obtained, was cooled slowly and crystallization started at 53° C. (after 30 min). Full crystallization occurred after ~1 h at 49° C. The mixture obtained was cooled to rt over a further 3 h with an ice bath and stirred at rt for a further 1.5 h. The precipitate obtained was collected and washed with acetone. An α-methylbenzylamine salt of cyclohex-3-ene-1-carboxylic acid as set out in the reaction scheme above was obtained.

Yield (wet): 1966.9 g; optical rotation: $^{20}[\alpha]_D=+8.05°$ (c=1, MeOH)

Step B. Salt Resolution 1966.9 g (wet) of a salt as set out under step A and 3.8 volumes of acetone were charged to a 10 L vessel and the mixture obtained was heated to 55 to 60° C. When the product had dissolved, the solution obtained was stirred for a further 15 min and then slowly cooled to rt. Crystallization started after 1 h 10 min (53° C.). The mixture obtained was cooled to 20 to 25° C. over 4.5 h and stirred at rt for a further 1.5 h. The precipitate obtained was filtered off and washed with acetone. An α-methylbenzylamine salt of cyclohex-3-ene-1-carboxylic acid wherein the R-isomer was enriched was obtained.

Yield (wet): 1143 g; optical rotation: $^{20}[\alpha]_D=+20.65°$ (c=1, MeOH)

Step B was repeated until a required optical rotation ($^{20}[\alpha]_D>40°$) was achieved.

Step C. Salt Break to Obtain cyclohex-3-ene-1(R)-carboxylic acid

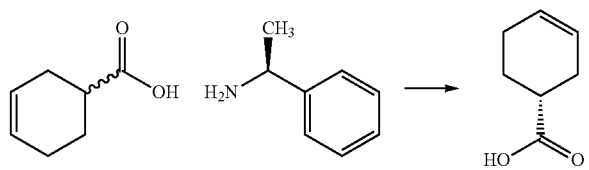

579.6 g of cyclohex-3-ene-1(R)-carboxylic acid (S)-(−)-α-methylbenzylamine salt and 5 volumes of MTBE were charged to a flask at 20-25° C. and the mixture obtained was stirred. To the mixture obtained 10 volumes of 1M HCl were added, the mixture obtained was stirred for 5-10 min and two layers were formed. The layers obtained were separated and the aqueous layer obtained was extracted with MTBE. The organic layers obtained were combined and washed with brine. The organic phase obtained was dried over $Na_2SO_4$, filtered, and the filter cake obtained was washed with MTBE. From the filtrate obtained solvent was removed in vacuo. Cyclohex-3-ene-1(R)-carboxylic acid in the form of a clear oil was obtained.

Yield: 301.78 g

Optical rotation $^{20}[\alpha]_D=+83.1°$ (c=1, $CHCl_3$)

Step D1. Curtius Rearrangement to Obtain tert-Butyl cyclohex-3-enyl-1(R)-carbamate

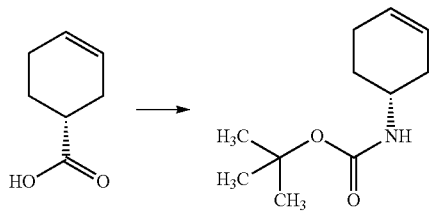

305 g of cyclohex-3-ene-1(R)-carboxylic acid and 10 volumes of toluene were charged to a flask at 20-25° C. and the mixture obtained was stirred. To the mixture obtained 1.1 equivalents of $(C_2H_5)_3N$ were added dropwise over 15 min and the mixture obtained was stirred for a further 20 min. To the mixture obtained 1.05 equivalents of DPPA were added dropwise over approximately 20 min and the temperature raised to 95° C. (exothermic reaction) with vigorous gas evolution. The mixture obtained was stirred for 15 min and heated to reflux. Progress of the reaction was followed by $^1H$ NMR measurements until completion. The mixture obtained was cooled to 80° C. over 35 min and 5 equivalents of tert-butanol were added dropwise over 10 min, followed by 7.65 g of CuCl. The mixture obtained was warmed to 100° C. and stirred for a further 40 min. Progress of the reaction was followed by $^1H$ NMR measurements until completion. The mixture obtained was cooled and 5 volumes of aqueous, saturated $NaHCO_3$ solution were added over 10 min. The mixture obtained was stirred for 20 min and left overnight. The mixture obtained was filtered and the residual solid was washed with toluene. The organic layers were separated and the aqueous layer was washed twice with toluene. All organic layers obtained were combined, washed with $H_2O$ and solvent was removed in vacuo. tert-Butyl cyclohex-3-enyl-1(R)-carbamate was obtained in the form of a light brown solid. Yield (crude): 479.7 g The crude tert-butyl cyclohex-3-enyl-1(R)-carbamate obtained was subjected to chromatography. For 160 g of crude product the column was packed with 1.5 Kg silica gel, using 2.5 L of cyclohexane, and topped with sand. The crude product was loaded in 0.8 L of 5% EtOAc/cyclohexane. The column was flashed with the following gradient system, a discrete fraction being collected each time:

2% EtOAc/cyclohexane (9×0.8 L fractions)

5% EtOAc/cyclohexane (7×0.8 L fractions)

10% EtOAc/cyclohexane (4×0.8 L fractions)

Overall yield after chromatography: 81.3% of theory $^1H$ NMR (500 MHz, $CDCl_3$, ppm): δ 5.64-5.67 (m, 1H), 5.56-5-60 (m, 1H), 4.54 (s, broad, 1H), 3.77 (s, broad, 1H), 2.32-2.34 (m, 1H), 2.07-2.17 (m, 2H), 1.81-1.87 (m, 2H), 1.48-1.56 (m, 1H), 1.44 (s, 9H).

$^{13}C$ NMR (500 MHz, $CDCl_3$, ppm): δ 155.3, 126.9, 124.5, 79.1, 45.7, 32.1, 28.4, 23.6.

In alternative to Step D1 above Step D2 below was carried out:

Step D2. Curtius Rearrangement via Acid Chloride to Obtain tert-Butyl cyclohex-3-enyl-1(R)-carbamate

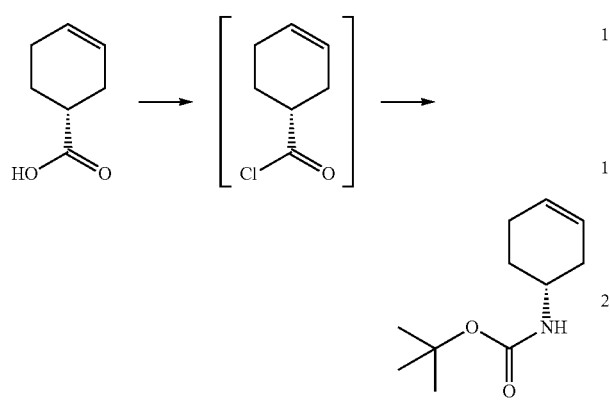

5 g of 3-cyclohexene-1(R)-carboxylic acid and 50 ml of CH$_2$Cl$_2$ were charged to a flask at 20-25° C. and the mixture obtained was stirred. To the mixture obtained 5.3 g of oxalyl chloride wee added followed by a drop of DMF. The mixture obtained was stirred at 20 to 25° C. for 1.5 h until HPLC determination showed reaction completeness. 35.8 mg of tetrabutylammonium bromide was added to the mixture obtained, the mixture obtained was cooled to <10° C. and 2.58 g of sodium azide in 10 ml of H$_2$O was added dropwise at <10° C. The mixture obtained was stirred at 0 to 5° C. for 2 h and followed by HPLC until reaction completion. Upon reaction completion the mixture obtained was warmed to 15 to 25° C., the phases obtained were separated, and the upper organic layer obtained was dried over anhydrous MgSO$_4$. MgSO$_4$ was removed by filtration, the filtrate obtained was returned to a vessel and 125.5 mg of CuCl was added followed by 7.35 g of tert-butanol. The mixture obtained was stirred at 20 to 25° C. overnight. To the mixture obtained a further portion of 7.35 g of tert-butanol was added and the mixture obtained was stirred once more overnight to ensure completion of the reaction. Upon completion of the reaction the mixture obtained was washed with 2×10 ml of 0.1 M HCl, 2×10 ml of 5% aqueous NaHCO$_3$ solution and 2×10 ml of H$_2$O, 15 ml of cyclohexane was added and solvent was removed in vacuo. Cyclohexane treatment was repeated, 7.5 ml of EtOAc was added and the mixture obtained was concentrated to dryness. 5.46 g of tert-Butyl cyclohex-3-enyl-1 (R)-carbamate was obtained.

$^1$H NMR (200 MHz, DMSO-d$_6$, ppm) δ 6.76 (d, J=7.8 Hz, 1H), 5.64-5.51 (m, 2H), 3.5-3.3 (m, 1H), 2.19-1.55 (m, 5H), 1.56-1.26 (m, 10H).

$^{13}$C NMR (50 MHz, DMSO-d$_6$, ppm) δ 154.9, 126.5, 125.2, 77.4, 45.8, 31.4, 28.8, 28.3, 24.5.

MS (ESI, g/mol): m/z 395 [2M+H]$^+$

Step E. Epoxidation to Obtain tert-Butyl (1R,3R,6S)-(7-oxa-bicyclo[4.1.0]hept-3-yl)-carbamate

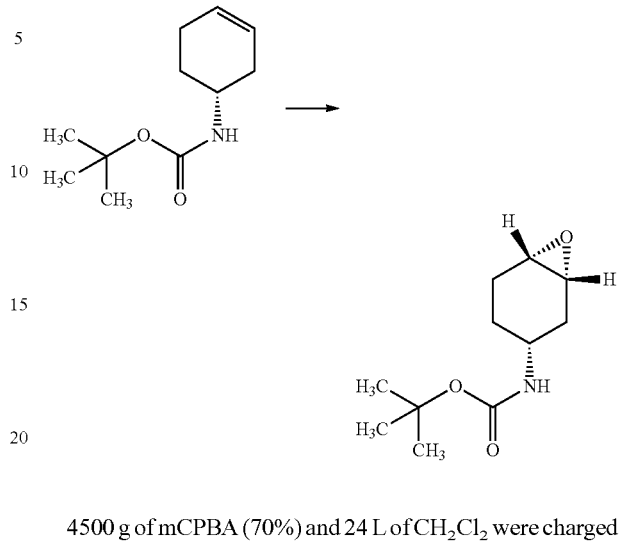

4500 g of mCPBA (70%) and 24 L of CH$_2$Cl$_2$ were charged to a vessel and the mixture obtained was cooled to 15° C. To the mixture obtained 3000 g of tert-butyl cyclohex-3-enyl-1 (R)-carbamate in 4.5 L of CH$_2$Cl$_2$ was added dropwise over approximately 30 min maintaining the temperature at 15 to 25° C. To the mixture obtained 1.5 L of CH$_2$Cl$_2$ was added and the mixture obtained was stirred at 20 to 25° C. for 1 h and heated to reflux (40° C.) for 2 h. Upon completion of the reaction ($^1$H NMR control), the mixture was cooled to −5 to 0° C., stirred overnight and the solid precipitate was isolated and washed with CH$_2$Cl$_2$. The resultant filtrate was washed with 10% sodium thiosulfate solution in order to remove peroxides, 10% aqueous NaHCO$_3$ solution until a pH>7 was achieved in the aqueous phase, and water. The organic phase obtained was concentrated to minimal volume, 5 L of toluene was added and the mixture obtained was concentrated again to minimal volume. This strip process was repeated two more times. tert-butyl (1R,3R,6S)-(7-Oxa-bicyclo[4.1.0]hept-3-yl)-carbamate in the form of a solution in toluene was obtained.

Yield (crude): 2.63 Kg (corresponds to 2.05 Kg yield corrected for residual mCBA and toluene).

$^1$H NMR (200 MHz, CDCl$_3$, ppm) δ 4.85 (d, J=7 Hz, 1H), 3.6-3.54 (m, 1H), 3.10 (s, broad, 2H), 2.23-1.99 (m, 2H), 1.92-1.67 (m, 2H), 1.54-1.27 (m, 11H).

Step F. Epoxide Ring Opening to Obtain {(1R,2R,4R)-4-[(tert-Butoxycarbonyl)-amino]-2-hydroxycyclohexyl}-benzene-carbothioate and {(1S,2S,5R)-5-[(tert-Butoxycarbonyl)-amino]-2-hydroxycyclohexyl}-benzene-carbothioate

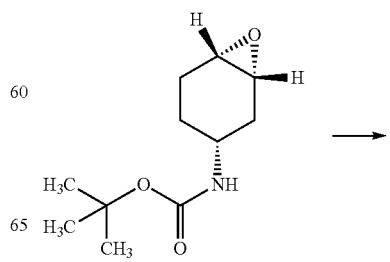

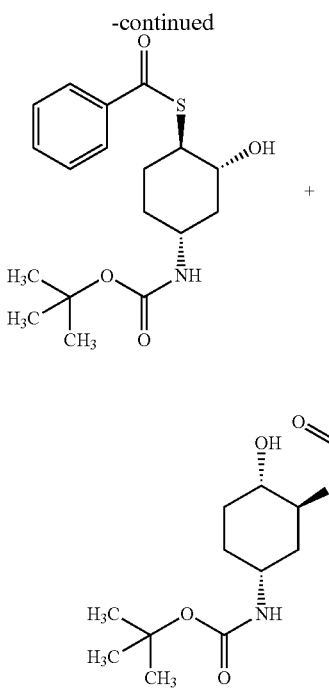

2630 g (2050 g corrected) of tert-butyl (1R,3R,6S)-(7-oxa-bicyclo[4.1.0]hept-3-yl)-carbamate in the form of a solution in toluene (solution weight 15.44 Kg) from Step E above and 3.1 L of toluene were charged to a vessel and the mixture obtained was stirred at 15-25° C. To the mixture obtained 1.44 L of thiobenzoic acid (90%) was added dropwise. The temperature was kept below 30° C. To the mixture obtained further 1.9 L of toluene and 85.3 g of tetrabutylammonium chloride monohydrate in one portion were added, external temperature control was stopped, and the mixture obtained was subjected to exotherm reaction. The mixture obtained was heated to 40-45° C. and stirred for 4 h. Upon completion of the reaction (TLC and $^1$H NMR-control), the mixture obtained was cooled to 15 to 20° C. and washed twice with 5% aqueous NaHCO$_3$ solution followed by twice with H$_2$O. The organic layer obtained was concentrated in vacuo to minimum volume. To the concentrate obtained 10.25 L of toluene was added and the mixture obtained was again concentrated to minimum volume. That process was repeated and the dry weight determined All subsequent reslurry volumes are relative to this determined weight. To the crude concentration residue obtained 0.5 volumes of toluene were added under stirring and the mixture obtained was stirred at 15 to 25° C. for 30 min. To the mixture obtained 0.5 volumes of heptane was added dropwise over 15 min and the mixture obtained was stirred at 15 to 25° C. for 40 min. The solid obtained was filtered and washed with 0.25 volumes of toluene-heptane (1:1), followed by a slurry wash 0.5 volumes of toluene-heptane 1:1, followed by a further displacement wash with 0.25 volumes of toluene-heptane 1:1. This procedure reduced the amount of unwanted regioisomer and of thiobenzoic acid to undetectable (by $^1$H NMR). The solid obtained was isolated and dried in vacuo at 30° C. 1094 g of {(1R,2R,4R)-4-[(tert-Butoxycarbonyl)-amino]-2-hydroxy-cyclohexyl}-benzene-carbothioate in the form of a white crystalline solid was obtained.

The unwanted regioisomer {(1S,2S,5R)-5-[(tert-Butoxycarbonyl)-amino]-2-hydroxy-cyclohexyl}-benzene-carbothioate, which remains in solution can be isolated via conventional methods, i.e. isolation via chromatography.

{(1R,2R,4R)-4-[(tert-Butoxycarbonyl)-amino]-2-hydroxy-cyclohexyl}-benzene-carbothioate $^1$H NMR (200 MHz, DMSO-d$_6$, ppm) δ 7.92-7.87 (m, 2H), 7.71-7.63 (m, 1H), 7.58-7.49 (m, 2H), 6.85 (d, J=8 Hz, 1H), 5.11 (d, J=5.6 Hz, 1H), 3.49-3.25 (m, 3H), 2.12-1.95 (m, 2H), 1.79-1.69 (m, 1H), 1.54-1.14 (m, 12H).

{(1S,2S,5R)-5-[(tert-Butoxycarbonyl)-amino]-2-hydroxy-cyclohexyl}-benzene-carbothioate $^1$H NMR (200 MHz, DMSO-d$_6$, ppm) δ 7.92 (d, 2H), 7.75-7.68 (m, 1H), 7.61-7.53 (m, 2H), 6.92 (d, J=7.6 Hz, 1H), 5.19 (d, J=3.2 Hz, 1H), 3.93-3.91 (m, 1H), 3.66 (m, 1H), 3.48-3.38 (m, 1H), 2.18-2.07 (m, 1H), 1.80-1.39 (m, 5H), 1.39 (s, 9H).

EXAMPLE 2

{(1R,2R,4R)-4-[(tert-Butoxycarbonyl)-amino]-2-hydroxy-cyclohexyl}-benzene-carbothioate via Telescoped Procedure

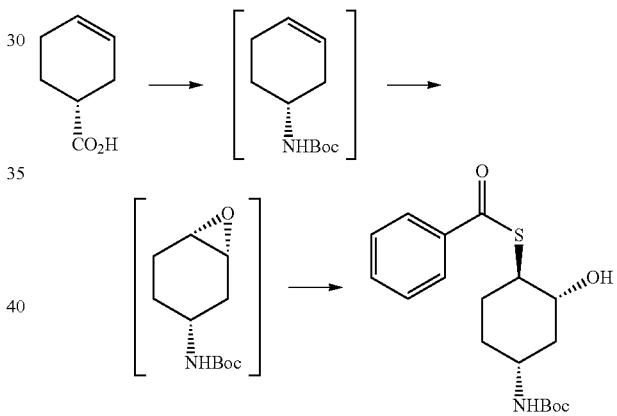

Step A. Curtius Rearrangement to obtain tert-butyl cyclohex-3-enyl-1(R)-carbamate To a solution of 150 g of cyclohex-3-ene-1(R)-carboxylic acid in 1275 mL of chlorobenzene was added 176.4 mL of (C$_2$H$_5$)$_3$N and rinsed through with 75 mL of chlorobenzene. The mixture obtained was heated to 78 to 82° C. and 327.2 g of DPPA was added cautiously, maintaining the temperature at 80 to 90 C, followed by 60 mL of chlorobenzene. The mixture obtained was stirred at 78 to 82° C. for 1 h and analyzed for reaction completion by TLC (absence of starting material). Upon reaction completion 441 g of tert-butanol in 102 mL of chlorobenzene was charged to the mixture obtained, maintaining the temperature at 70 to 80° C. 4.71 g of CuCl in 48 mL of chlorobenzene was added to the mixture obtained, followed by 27 mL of chlorobenzene as a line rinse. The mixture obtained was stirred at 90 to 95° C. for 2 h and analyzed for reaction completion by TLC (formation of product). Upon reaction completion, the mixture obtained was cooled to 15 to 25° C., washed with 1500 mL of 20% aqueous K$_2$CO$_3$ solution, filtered through celite and rinsed with 150 mL of chlorobenzene to give a three phase mixture. The phases obtained were separated and the upper layer was washed again with 1500 mL of 20% aqueous K$_2$CO$_3$ solution, again giving three layers which were separated. The combined middle phases obtained were extracted with 300 mL of chlorobenzene, the upper layer then being combined with the previous upper layer and washed with 1500 mL of 20% aqueous K$_2$CO$_3$ solution. The organic layer obtained was washed with 0.5 M H$_3$PO$_4$ (2×1500 mL) followed by 1500 mL of 5% aqueous NaCl solution. The content of the step A product tert-Butyl cyclohex-3-enyl-1(R)-carbamate in solution is determined via NMR or HPLC.

Step B. Epoxidation to obtain tert-butyl (1R,3R,6S)-(7-oxa-bicyclo[4.1.0]hept-3-yl)-carbamate A mixture of the Curtius solution obtained in step A in chlorobenzene (189.3 g olefinic material; assuming all tert-butyl cyclohex-3-enyl-1(R)-carbamate) with 190 mL of chlorobenzene was cooled to 10 to 15° C. and 284.0 g of 70% mCPBA was added in portions, maintaining the reaction temperature below 30° C. The mixture obtained was stirred at 20 to 25° C. for 1 h and the reaction was analyzed for completion by NMR (absence of starting material). Upon reaction completion the mixture was heated to 38 to 42° C., stirred for 2 h and analyzed for completion by NMR (absence of trans-epoxide).

Upon completion, the reaction mixture was cooled to −5 to 0° C., filtered and rinsed through with chlorobenzene (2×95 mL), warmed to 15 to 25° C. and washed with 10% aqueous sodium thiosulfate solution (2×946.5 mL) followed by 5% aqueous NaHCO$_3$ solution (3×946.5 mL) and finally H$_2$O (2×946.5 mL). The content of the step B product tert-butyl (1R,3R,6S)-(7-oxa-bicyclo[4.1.0]hept-3-yl)-carbamate in solution is determined via NMR or HPLC.

Step C. Epoxide Ring-Opening to Obtain {(1R,2R,4R)-4-[(tert-butoxycarbonyl)-amino]-2-hydroxy-cyclohexyl}-benzene-carbothioate A solution of 124.9 g of tert-butyl (1R,3R,6S)-(7-oxa-bicyclo[4.1.0]hept-3-yl)-carbamate from step B in 25 ml of chlorobenzene was degassed with argon for 30 min and the mixture obtained was adjusted to 15 to 20° C. To the mixture obtained 88.0 mL of 90% thiobenzoic acid was charged dropwise, maintaining the temperature below 30° C., followed by 37 mL of chlorobenzene and 5.2 g of tetrabutylammonium chloride monohydrate, maintaining the temperature below 30° C. The mixture obtained was stirred at 40 to 45° C. for 4 h and analyzed for reaction completion by NMR (absence of epoxide starting material).

Upon reaction completion the mixture obtained was cooled to 15 to 20° C. and washed with 5% aqueous NaHCO$_3$ solution (2×625 mL) followed by H$_2$O (2×625 mL).

The mixture obtained was concentrated at less than 45° C. to approximately 6.8 volumes and stirred at 20 to 25° C. until crystallization initiated. To the mixture obtained 333 mL of heptane was added dropwise and the mixture obtained was stirred for a further 30 min. To the mixture obtained again 333 mL of heptane was added dropwise, followed by a further 30 min stirring at 20 to 25° C., and a final heptane charge of 333 mL was added. The mixture obtained was stirred at 20 to 25° C. for ca. 13 h. The mixture obtained was filtered, the resultant filter cake was washed with toluene-heptane (1:1, 4×124 mL) and dried in vacuo at <40° C. {(1R,2R,4R)-4-[(tert-Butoxycarbonyl)-amino]-2-hydroxy-cyclohexyl}-benzene-carbothioate in the form of an off-white crystalline solid was obtained.

Overall yield (from 150 g of cyclohex-3-ene-1(R)-carboxylic acid): 75.2 g

The $^1$H NMR pattern confirms the structure of {(1R,2R,4R)-4-[(tert-butoxycarbonyl)-amino]-2-hydroxy-cyclohexyl}-benzene-carbothioate. The NMR pattern for {(1R,2R,4R)-4-[(tert-Butoxycarbonyl)-amino]-2-hydroxy-cyclohexyl}-benzene-carbothioate is described in example 1, step F.

EXAMPLE 3

{(1R,2R,4R)-4-[(2,2,2-Trifluoro-acetyl)-amino]-2-hydroxy-cyclohexyl}-benzene-carbothioate Step A1. Curtius Rearrangement via DPPA to Obtain N-(cyclohex-3-en-1(R)-yl)-2,2,2-trifluoro-acetamide

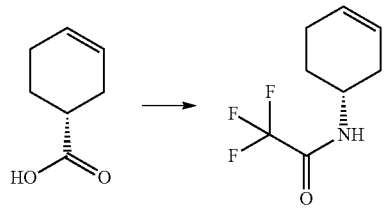 [SMILES: O=C(O)[C@H]1CC=CCC1 ; O=C(N[C@H]1CC=CCC1)C(F)(F)F]

5 g of 3-cyclohexene-1(R)-carboxylic acid and 42.5 ml of chlorobenzene were charged to a flask at 20-25° C. and the mixture obtained was stirred. To the mixture obtained 11.2 ml of (C$_2$H$_5$)$_3$N was added dropwise, followed by 2.6 ml of chlorobenzene. The mixture obtained was warmed to 78 to 82° C. and 10.9 g of DPPA was added in a dose controlled fashion, maintaining the temperature at 80 to 90° C. and steady gas evolution. A 2.1 ml of chlorobenzene line rinse was given. The mixture obtained was stirred at 78 to 82° C. for 1 h until reaction completion determined by TLC. To the mixture obtained 22.6 g of CF$_3$COOH in 3.4 ml of chlorobenzene was added dropwise maintaining the temperature at 70 to 80° C., followed by 157 mg of CuCl in 1.6 ml of chlorobenzene and a 0.9 ml of chlorobenzene line rinse. The mixture obtained was stirred at 90 to 95° C. for 2 h and followed by TLC until reaction completion. The mixture obtained was cooled to 15 to 25° C. and 50 ml of 20% aqueous K$_2$CO$_3$ solution was added. The mixture obtained was stirred for 15 min, filtered through celite to remove the residual solid and the solid was washed with 5 ml of chlorobenzene. The layers obtained were separated and the upper organic layer obtained was washed again with 50 ml of 20% aqueous K$_2$CO$_3$ solution. The combined aqueous layers obtained were back extracted with 10 ml of chlorobenzene and the combined organic phases were washed with 50 ml of 25% aqueous NaCl solution, 2×50 ml of 0.5M H$_3$PO$_4$ and 50 ml of 5% aqueous NaCl solution. Solvent was removed in vacuo to give a light brown solid. Crude material (6.63 g) was subjected to purification by column chromatography (cyclohexane-EtOAc 9:1) to obtain 5.10 g of N-(cyclohex-3-en-1(R)-yl)-2,2,2-trifluoro-acetamide in the form of a crystalline white solid.

$^1$H NMR (200 MHz, DMSO-d$_6$, ppm) δ 9.33 (d, 1H), 5.69-5.56 (m, 2H), 3.82 (s, broad, 1H), 2.25-1.96 (m, 4H), 1.81-1.74 (m, 1H), 1.66-1.58 (m, 1H).

$^{13}$C NMR (50 MHz, DMSO-d$_6$, ppm) δ 155.9+155.2, 126.6, 124.5, 118.8+113.1, 45.8, 30.1, 27.5, 24.3.

MS (ESI, g/mol): m/z 194 [M+H]$^+$

In the alternative to Step A1 as described above, Step A2 as described below was carried out:

Step A2. N-(cyclohex-3-en-1(R)-yl)-2,2,2-trifluoro-acetamide via base

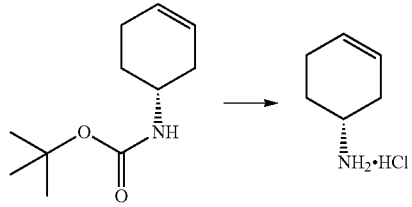

16.3 g of tert-Butyl cyclohex-3-enyl-1(R)-carbamate and 206.5 ml of 4 M HCl in dioxane were charged to a flask at 20-25° C. and the mixture obtained was stirred until reaction completion determined by TLC. The mixture obtained was concentrated to approximately one third of the volume and 200 ml of diethyl ether was added and the mixture obtained was stirred for 5 min. The mixture obtained was filtered and the solid obtained was washed twice with 10 ml of diethyl ether and dried under high vacuum. 10.73 g of 3-cyclohexene-1(R)-amine hydrochloride in the form of a crystalline white solid was obtained.

$^1$H NMR (200 MHz, DMSO-d$_6$, ppm) δ 8.36 (s, 2H), 5.68-5.52 (m, 2H), 3.18-3.09 (s, broad, 1H), 2.38-2.30 (m, 1H), 2.16-1.93 (m, 4H), 1.68-1.63 (m, 1H).

$^{13}$C NMR (50 MHz, DMSO-d$_6$, ppm) δ 126.7, 123.4, 46.3, 29.0, 26.0, 23.4.

MS (ESI, g/mol): m/z 98 [M (free base)+H]$^+$

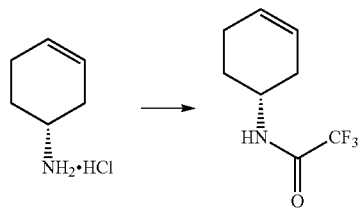

5 g of 3-cyclohexene-1(R)-amine hydrochloride and 50 ml of CH$_2$Cl$_2$ were charged to a flask at rt and stirred. To the mixture obtained 7.8 ml of (C$_2$H$_5$)$_3$N was added dropwise and stirred for 10 min, followed by 8.25 g of trifluoroacetic anhydride and the mixture obtained was stirred until reaction completion, determined by TLC. The mixture obtained was washed with 50 ml of 0.1 M HCl followed by 50 ml of 5% NaHCO$_3$ and 50 ml of H$_2$O, and concentrated to dryness. 7.02 g of N-(cyclohex-3-en-1(R)-yl)-2,2,2-trifluoro-acetamide in the form of a pale white crystalline solid was obtained.

The $^1$H and $^{13}$C NMR pattern confirm the structure of N-(cyclohex-3-en-1(R)-yl)-2,2,2-trifluoro-acetamide. The NMR spectra and the MS for N-(cyclohex-3-en-1(R)-yl)-2,2,2-trifluoro-acetamide are described in example 3, step A1

Step B. Epoxidation to Obtain 2,2,2-Trifluoro-N-(1R,3R,6S)-(7-oxa-bicyclo[4.1.0]hept-3-yl)-acetamide

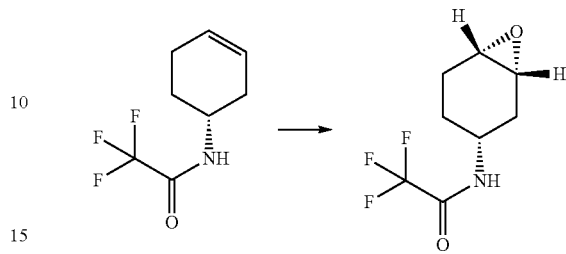

9.2 g of mCPBA (70%) was charged to a vessel containing a cooled (10-15° C.) solution of 6 g of N-(cyclohex-3-en-1(R)-yl)-2,2,2-trifluoro-acetamide in 60 ml of chlorobenzene maintaining the temperature <30° C., and rinsed through with 3 ml of chlorobenzene. The mixture obtained was stirred at 20 to 25° C. for 1 h and the reaction was followed by TLC until completion. Upon completion of the reaction, the mixture obtained was heated to 38 to 42° C. for 2 h until reaction completion and cooled to 0 to –5° C., stirred for 30 min and the solid precipitate (mCBA) was filtered off and washed through with 2×3 ml of chlorobenzene. The resultant filtrate was washed with 30 ml of 10% sodium thiosulfate solution to remove peroxides, 2×30 ml of 5% NaHCO$_3$ solution to ensure an pH of aqueous phase of >7, and 30 ml of H$_2$O. The mixture obtained was concentrated to dryness. 5.08 g of 2,2,2-Trifluoro-N-(1R,3R,6S)-(7-oxa-bicyclo[4.1.0]hept-3-yl)-acetamide containing ca. 8% of anti (trans) epoxide in the form of a crystalline white solid was obtained.

$^1$H NMR (400 MHz, DMSO-d$_6$, ppm) δ 9.21 (d, J=7.2 Hz, 1H), 3.80-3.52 (m, 1H, H-1), 3.10-3.09 (m, 2H), 2.22-1.66 (m, 4H), 2.03-2.10 (m, 1H), 1.91-1.78 (m, 1H), 1.76-1.68 (m, 1H), 1.52-1.30 (m, 2H).

$^{13}$C NMR (100 MHz, DMSO-d$_6$, ppm) δ 155.8 & 155.1, 118.8 & 113.1, 51.0, 50.1, 44.6, 28.9, 23.6, 23.6.

MS (ESI, g/mol): m/z 208 [M−H]$^-$

Step C. Epoxide Ring Opening to Obtain {(1R,2R,4R)-4-[(2,2,2-Trifluoro-acetyl)-amino]-2-hydroxy-cyclohexyl}-benzene-carbothioate

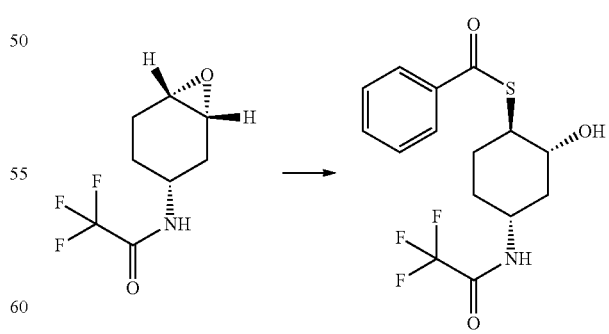

A 115 ml solution containing 8.8 g of 2,2,2-trifluoro-N-(1R,3R,6S)-(7-oxa-bicyclo[4.1.0]hept-3-yl)-acetamide in chlorobenzene was charged to a vessel and the mixture obtained was stirred at 15-25° C. giving a clear yellow solution which was degassed with argon for 15 minutes. To the mixture obtained 7.45 g of thiobenzoic acid was added dropwise ensuring a temperature below 30° C. followed by 1.1 ml of chlorobenzene as a line rinse. 368 mg of tetrabutylammonium chloride monohydrate was added in portions at <30° C. The mixture obtained was heated to 40-45° C., stirred and the reaction was followed by TLC determination until completion. Upon completion of the reaction, the mixture obtained was cooled to 15 to 25° C., filtered, the filter cake obtained was washed with 10 ml of chlorobenzene and dried in vacuo at <40° C.

8.75 g of {(1R,2R,4R)-4-[(2,2,2-Trifluoro-acetyl)-amino]-2-hydroxy-cyclohexyl}-benzene-carbothioate in crystalline form was obtained.

$^{1}$H NMR (200 MHz, DMSO-$d_{6}$, ppm) δ 9.38 (s, 1H), 7.91 (m, 2H), 7.68 (m, 1H), 7.55 (m, 2H), 5.23 (s, 1H), 3.80 (m, 1H), 3.55-3.49 (m, 1H), 3.41-3.34 (m, 1H), 2.13-2.03 (m, 2H), 1.82-1.79 (m, 1H), 1.60-1.38 (m, 3H).

$^{13}$C NMR (50 MHz, DMSO-$d_{6}$, ppm) δ 191.1, 155.8+155.0, 136.8, 133.7, 129.1, 126.7, 118.8+113.1, 68.3, 49.4, 46.8, 40.8, 30.8, 29.6.

MS (ESI, g/mol): 348 [M+H]$^{+}$

EXAMPLE 4

{(1R,2R,4R)-4-[(2,2,2-Trifluoro-acetyl)-amino]-2-hydroxy-cyclohexyl}-benzene-carbothioate via Telescoped Procedure

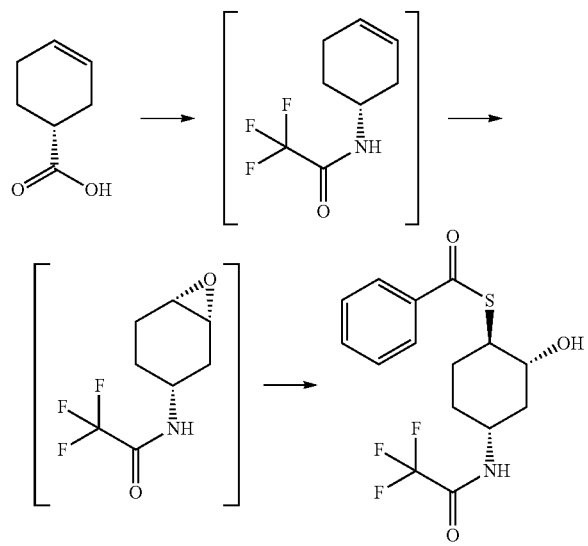

Step A: N-(Cyclohex-3-en-1(R)-yl)-2,2,2-trifluoro-acetamide 50 g of 3-cyclohexene-1(R)-carboxylic acid and 425 ml of chlorobenzene were charged to a flask at 20-25° C. and the mixture obtained was stirred. To the mixture obtained 110 ml of $(C_{2}H_{5})_{3}N$ was added dropwise, followed by 25 ml of chlorobenzene. The mixture obtained was warmed to 78 to 82° C. and 109.2 g of DPPA was added in a dose controlled fashion, maintaining the temperature at 80 to 90° C. and steady gas evolution. A 20 ml chlorobenzene line rinse was given. The mixture obtained was stirred at 78 to 82° C. for 1 h until complete (determined by TLC). The mixture obtained was cooled to approximately 70° C. and 226 g of $CF_{3}COOH$ in 34 ml of chlorobenzene was added dropwise maintaining the temperature at 70 to 80° C., followed by 1.57 g of CuCl and a 25 ml chlorobenzene line rinse. The mixture obtained was stirred at 90 to 95° C. for 2 h and the reaction was followed by TLC. Upon reaction completion the mixture obtained was cooled to 15 to 25° C., 375 ml of 20% aqueous $K_{2}CO_{3}$ solution was added and the mixture obtained was stirred for 15 min. The layers obtained were separated and to the upper organic layer obtained was added 375 ml of 20% aqueous $K_{2}CO_{3}$ solution. The mixture obtained was filtered through celite to remove the residual solid and the solid was washed with 50 ml of chlorobenzene. The layers obtained were separated and the combined lower aqueous layers obtained were then back extracted with 250 ml of chlorobenzene, separated, and the combined organic phases obtained were washed with 500 ml of 0.5 M $H_{3}PO_{4}$. The aqueous layer obtained was back extracted with 300 ml of chlorobenzene and the combined organic phases obtained were washed with 500 ml of 5% aqueous NaCl solution.

A strip weight assay was carried out to determine the N-(cyclohex-3-en-1(R)-yl)-2,2,2-trifluoro-acetamide content. The chlorobenzene solution contained 69.52 g of N-(cyclohex-3-en-1(R)-yl)-2,2,2-trifluoro-acetamide and was used in the following epoxidation step (Step B below).

The $^{1}$H NMR pattern confirms the structure of N-(cyclohex-3-en-1(R)-yl)-2,2,2-trifluoro-acetamide. The NMR pattern and the MS for N-(cyclohex-3-en-1(R)-yl)-2,2,2-trifluoro-acetamide are described in example 3, step A1.

Step B: 2,2,2-Trifluoro-N-(1R,3R,6S)-(7-oxa-bicyclo[4.1.0]hept-3-yl)-acetamide 106.5 g of m-Chloroperbenzoic acid (70%) was charged in portions to the cooled (10-15° C.) solution of 69.5 g of the N-(cyclohex-3-en-1(R)-yl)-2,2,2-trifluoro-acetamide from Step A above maintaining the temperature <30° C., and rinsed through with 69.5 ml of chlorobenzene. The mixture obtained was stirred at 20 to 25° C. for 1 h and the reaction was followed by TLC until completion. Upon reaction completion, the batch was cooled to 0 to -5° C., stirred for 30 min and the solid precipitate (mCBA) was filtered off and washed through with 2×34.8 ml of chlorobenzene. The resultant filtrate was then washed with 347.6 ml of 10% sodium thiosulfate solution to remove peroxides, and the resultant aqueous layer was back extracted with 208.6 ml of chlorobenzene. The combined organic layers obtained were washed with 347.6 ml of 5% $NaHCO_{3}$ solution to ensure a pH of >7 in the aqueous phase and the resultant aqueous layer was back extracted with 208.6 ml of chlorobenzene. The combined organic layers obtained were washed with 347.6 ml of $H_{2}O$.

A strip weight assay was carried out to determine the 2,2,2-Trifluoro-N-(1R,3R,6S)-(7-oxa-bicyclo[4.1.0]hept-3-yl)-acetamide content for use in ring-opening step (Step C). The chlorobenzene solution contained 58.64 g of 2,2,2-Trifluoro-N-(1R,3R,6S)-(7-oxa-bicyclo[4.1.0]hept-3-yl)-acetamide containing approximately 11% of anti (trans) epoxide. The $^{1}$H NMR pattern confirms the structure of 2,2,2-trifluoro-N-(1R,3R,6S)-(7-oxa-bicyclo[4.1.0]hept-3-yl)-acetamide. The NMR pattern and the MS for 2,2,2-trifluoro-N-(1R,3R,6S)-(7-oxa-bicyclo[4.1.0]hept-3-yl)-acetamide are described in example 3, step B.

Step C: {(1R,2R,4R)-4-[(2,2,2-Trifluoro-acetyl)-amino]-2-hydroxy-cyclohexyl}-benzene-carbothioate The chlorobenzene solution containing 58.64 g of 2,2,2-trifluoro-N-(1R,3R,6S)-(7-oxa-bicyclo[4.1.0]hept-3-yl)-acetamide was concentrated to approximately 5 volumes based upon epoxide. The concentrate obtained was degassed at 15-25° C. with argon for 30 min and the temperature was adjusted to 15 to 20° C. To the mixture obtained 58.1 g of thiobenzoic acid (90%) was added dropwise ensuring a temperature below 30° C. 17.6 ml of chlorobenzene was then charged to the vessel as a line rinse. To the mixture obtained 2.49 g of tetrabutylammonium chloride monohydrate was added in portions at <30° C. The mixture obtained was heated to 40-45° C. and stirred. The reaction was followed by TLC until completion. Upon reaction completion, the mixture obtained was cooled to 0 to 5° C., stirred for 1 h and filtered. The filter cake obtained was washed with 2×58.6 ml of chlorobenzene, and dried in vacuo at <40° C. 45.5 g of {(1R,2R,4R)-4-[(2,2,2-Trifluoro-acetyl)-amino]-2-hydroxy-cyclohexyl}-benzene-carbothioate was obtained in the form of a crystalline solid.

The $^1$H NMR pattern confirms the structure of {(1R,2R,4R)-4-[(2,2,2-Trifluoro-acetyl)-amino]-2-hydroxy-cyclohexyl}-benzene-carbothioate. The NMR pattern and the MS for {(1R,2R,4R)-4-[(2,2,2-Trifluoro-acetyl)-amino]-2-hydroxy-cyclohexyl}-benzene-carbothioate are described in example 3, step C.

EXAMPLE 5

Ethyl cyclohex-3-enyl-1(R)-carbamate

Step A1. Curtius Rearrangement via DPPA to Obtain Ethyl cyclohex-3-enyl-1(R)-carbamate

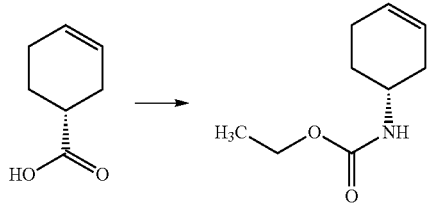

5 g of 3-cyclohexene-1(R)-carboxylic acid and 42.5 ml of chlorobenzene was charged to a flask at 20-25° C. and the mixture obtained was stirred. To the mixture obtained 11.2 ml of $(C_2H_5)_3N$ was added dropwise followed by 2.6 ml of chlorobenzene. The mixture obtained was warmed to 78 to 82° C. and 10.9 g of DPPA were added in a dose controlled fashion, maintaining the temperature at 80 to 90° C. and steady gas evolution. A 2.1 ml of chlorobenzene line rinse was given. The mixture obtained was stirred at 78 to 82° C. for 1 h until reaction completion (determined by TLC). Upon reaction completion to the mixture obtained 9.12 g of ethanol in 3.4 ml of chlorobenzene was added dropwise maintaining the temperature at 70 to 80° C., followed by 157 mg of CuCl in 1.6 ml of chlorobenzene and a 0.9 ml of chlorobenzene line rinse. The mixture obtained was stirred at 90 to 95° C. for 70 min and the reaction was followed by TLC determination until completion. Upon reaction completion the mixture obtained was cooled to 15 to 25° C. and 50 ml of 20% aqueous $K_2CO_3$ solution was added. The mixture obtained was stirred for 15 min, filtered through celite to remove the residual solid and the solid obtained was washed with 5 ml of chlorobenzene. The resulting three layers were separated and the upper organic layer obtained was washed with 50 ml of 20% aqueous $K_2CO_3$ solution. The combined middle layers obtained were back extracted with 10 ml of chlorobenzene and the combined upper phases obtained were washed with 50 ml of 25% aqueous NaCl solution, 2×50 ml of 0.5 M $H_3PO_4$ and 50 ml of 5% aqueous NaCl solution. From the mixture obtained solvent was removed in vacuo.

Crude ethyl cyclohex-3-enyl-1(R)-carbamate in the form of a light brown solid (6.40 g) was obtained and was subjected to purification by column chromatography (cyclohexane-EtOAc 9:1).

5.34 g of purified ethyl cyclohex-3-enyl-1(R)-carbamate was obtained.

$^1$H NMR (DMSO-$d_6$, 200 MHz, ppm): δ 7.05 (d, J=7.4 Hz, 1H), 5.65-5.51 (m, 2H), 4.02-3.91 (q, 2H), 3.57-3.44 (s, broad, 1H), 2.22-2.04 (m, 3H), 1.93-1.72 (m, 2H), 1.48-1.22 (m, 1H), 1.15 (t, J=7.0 Hz, 3H).

$^{13}$C NMR (DMSO-$d_6$, 50 MHz, ppm): δ 155.8, 126.5, 125.0, 59.4, 46.2, 31.4, 28.7, 24.4, 14.7.

MS (ESI, g/mol): m/z 170 [M+H]$^+$.

Alternatively to Step A1 above Step A2 below was carried out.

Step A2. Ethyl cyclohex-3-enyl-1(R)-carbamate via Base

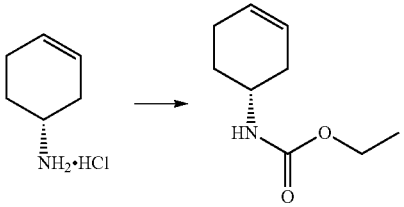

2 g of Cyclohex-3-enyl-1(R)-amine hydrochloride (Example 3, Step A2) and 20 ml of $CH_2Cl_2$ were charged to a flask at RT and the mixture obtained was stirred. To the mixture obtained 3.1 ml of $(C_2H_5)_3N$ was added dropwise, the mixture obtained was stirred for 10 min followed by addition of 1.5 ml of ethyl chloroformate and the mixture obtained was stirred until reaction completion (determined by TLC). The mixture obtained was washed with 0.1 M HCl, followed by 5% NaHCO$_3$ and H$_2$O and concentrated to dryness. 2.03 g of ethyl cyclohex-3-enyl-1(R)-carbamate in the form of a pale white crystalline solid was obtained.

The $^1$H and $^{13}$C NMR pattern confirm the structure of ethyl cyclohex-3-enyl-1(R)-carbamate. The NMR spectra and the MS for ethyl cyclohex-3-enyl-1(R)-carbamate are described in example 5, step A1.

EXAMPLE 6

2-(Cyclohex-3-en-1(R)-yl)-isoindole-1,3-dione

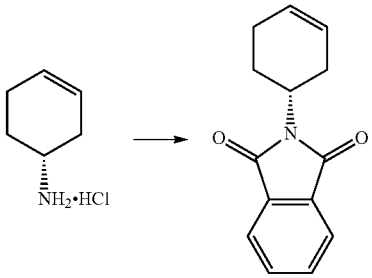

1 g of Cyclohex-3-enyl-1(R)-amine hydrochloride (Example 3 Step A2) and 40 ml of toluene was charged to a flask at RT and the mixture obtained was stirred. To the mixture obtained 1.9 ml of (C₂H₅)₃N was added dropwise, the mixture obtained was stirred for 10 min followed by 1.12 g of phthalic anhydride and the mixture obtained was heated to reflux, with H₂O removed under Dean-Stark conditions, until reaction completion (determined by HPLC). The mixture obtained was washed with 0.1 M HCl followed by 5% NaHCO₃ and H₂O, dried over Na₂SO₄ and concentrated to dryness. 1.20 g of 2-(cyclohex-3-en-1(R)-yl)-isoindole-1,3-dione in the form of a pale white crystalline solid was obtained.

$^1$H NMR (DMSO-$d_6$, 200 MHz, ppm): δ 7.85-7.70 (m, 4H), 5.73-5.60 (m, 2H), 4.31-4.15 (m, broad, 1H), 2.81-2.67 (m, 1H), 2.42-2.05 (m, 4H), 1.81-1.75 (m, 1H).

$^{13}$C NMR (DMSO-$d_6$, 50 MHz, ppm): δ 167.6, 134.1, 131.4, 126.4, 124.8, 122.8, 46.6, 28.1, 25.7, 25.2.

MS (ESI, g/mol): m/z 228 [M+H]⁺

EXAMPLE 7 tert-Butyl [(1R,3R,4R)-3-hydroxy-4-tritylsulfanyl-cyclohexyl]-carbamate and tert-Butyl [(1R,3S,4S)-4-hydroxy-3-tritylsulfanyl-cyclohexyl]-carbamate

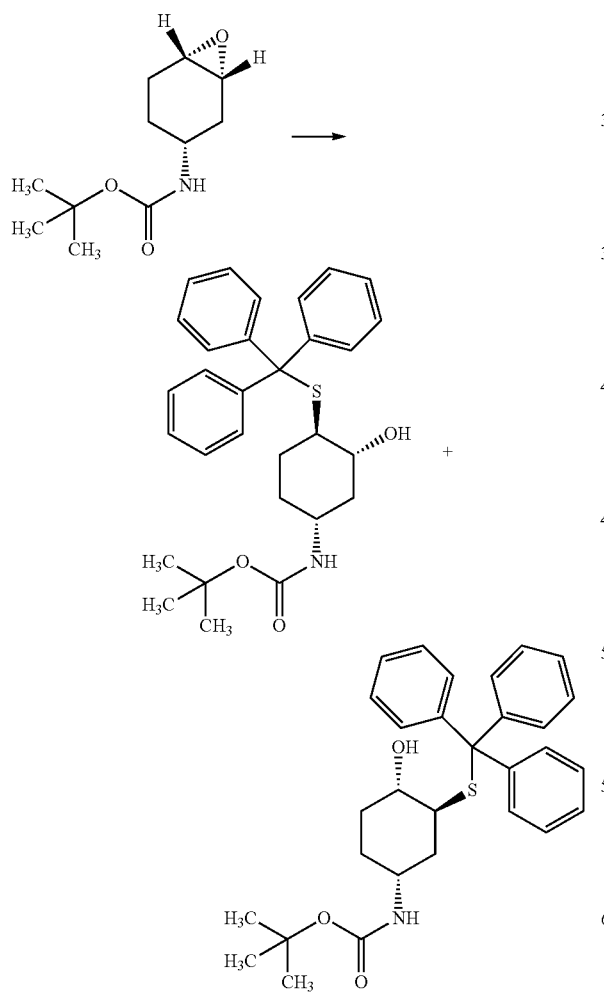

1 g of tert-butyl (1R,3R,6S)-(7-oxa-bicyclo[4.1.0]hept-3-yl)-carbamate (Example 1 Step E), 1.56 g of triphenyl-methanethiol, and 16.4 mL of acetonitrile were charged to a flask. To the mixture obtained 560 μL of DBN was added, and the mixture obtained was heated to 40° C. and stirred for 22.5 h. Upon completion of the reaction (TLC), the mixture obtained was cooled to rt, diluted with EtOAc, and washed with H₂O and brine. The organic layer obtained was dried over MgSO₄, concentrated in vacuo and the crude product obtained was subjected to column chromatography (eluent: cyclohexane/EtOAc 5:1). The required fractions were identified, combined and concentrated in vacuo.

1.11 g of tert-butyl [(1R,3R,4R)-3-hydroxy-4-tritylsulfanyl-cyclohexyl]-carbamate and 389 mg of tert-butyl [(1R,3S,4S)-4-hydroxy-3-tritylsulfanyl-cyclohexyl]-carbamate in the form of white solids were obtained.

tert-butyl [(1R,3R,4R)-3-hydroxy-4-tritylsulfanyl-cyclohexyl]-carbamate $^1$H NMR (200 MHz, DMSO-$d_6$, ppm, inter alia) δ 7.6-7.1 (m, 15H), 6.54 (d, J=8 Hz, 1H), 5.23 (d, J=4 Hz, 1H), 3.4-3.05 (m, 2H), 2.2-1.8 (m, 2H), 1.4-0.5 (m, 14H)

tert-butyl [(1R,3S,4S)-4-hydroxy-3-tritylsulfanyl-cyclohexyl]-carbamate $^1$H NMR (200 MHz, DMSO-$d_6$, ppm, inter alia) δ 7.5-7.15 (m, 15H), 6.6 (d, J=8 Hz, 1H), 4.55 (d, 1H), 3.5-3.1 (m, 2H), 1.7-0.9 (m, 15H)

MS (ESI, g/mol): m/z 534 [M+HCOO]⁻

EXAMPLE 8

2,2,2-Trifluoro-N-((1R,3R,4R)-3-hydroxy-4-tritylsulfanyl-cyclohexyl)-acetamide and 2,2,2-Trifluoro-N-((1R,3S,4S)-4-hydroxy-3-tritylsulfanyl-cyclohexyl)-acetamide

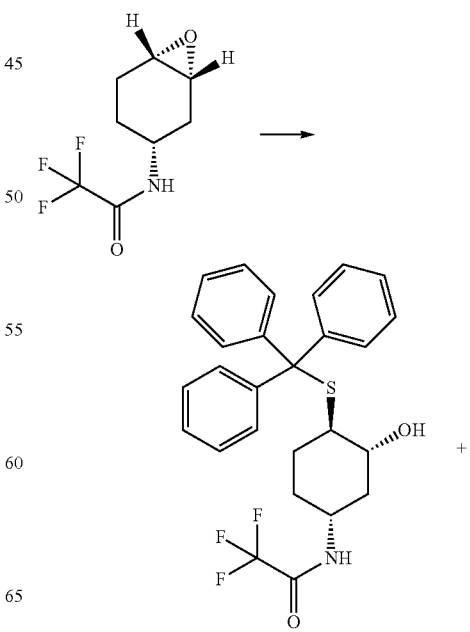

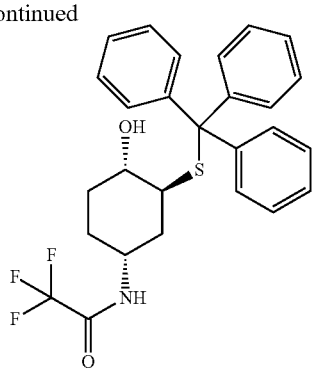

1.55 g of 2,2,2-Trifluoro-N-(1R,3R,6S)-7-oxa-bicyclo[4.1.0]hept-3-yl-acetamide (Example 3 Step B), 2.46 g of triphenylmethanethiol and 25 mL of acetonitrile were charged to a flask. To the mixture obtained 880 µL of DBN was added, and the mixture obtained was heated to 60° C. and stirred for 23 h. Upon completion of the reaction (TLC), the mixture obtained was cooled to rt, diluted with EtOAc and washed with H₂O and brine. The organic layer obtained was dried over MgSO₄, concentrated in vacuo and the crude product obtained was subjected to column chromatography (eluent: Cyclohexane/EtOAc 5:1). The required fractions were identified, combined and concentrated in vacuo.

1.856 g of 2,2,2-trifluoro-N-((1R,3R,4R)-3-hydroxy-4-tritylsulfanyl-cyclohexyl)-acetamide and 415 mg of 2,2,2-trifluoro-N-((1R,3S,4S)-4-hydroxy-3-tritylsulfanyl-cyclohexyl)-acetamide in the form of white solids were obtained.

2,2,2-Trifluoro-N-((1R,3R,4R)-3-hydroxy-4-tritylsulfanyl-cyclohexyl)-acetamide

¹H NMR (200 MHz, DMSO-d₆, ppm) δ 9.04 (d, J=7 Hz, 1H), 7.6-7.1 (m, 15H), 5.40 (d, J=4.6 Hz, 1H), 3.75-3.5 (m, 1H), 3.45-3.25 (m, 1H), 2.2-1.85 (m, 2H), 1.45-1.15 (m, 2H), 1.0-0.65 (m, 3H)

2,2,2-Trifluoro-N-((1R,3S,4S)-4-hydroxy-3-tritylsulfanyl-cyclohexyl)-acetamide

¹H NMR (200 MHz, DMSO-d₆, ppm) δ 9.17 (d, J=8 Hz, 1H), 7.45-7.1 (m, 15H), 4.86 (d, J=3 Hz, 1H), 4.00-3.75 (m, 1H), 3.6-3.45 (m, 1H), 1.8-0.65 (m, 7H)
MS (ESI, g/mol): m/z 484 [M−H]⁻

The invention claimed is:

1. A compound of formula I

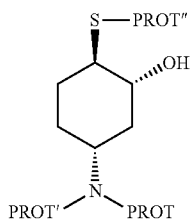

wherein
PROT is selected from
ethoxycarbonyl,
2,2,2-trifluoroacetyl, and
PROT' is hydrogen; or PROT and PROT' together with the nitrogen atom to which they are attached form a heterocyclic ring as an amine protecting group, and
PROT" is a thiol protecting group.

2. A compound according to claim 1, wherein
PROT is selected from
ethoxycarbonyl,
2,2,2-trifluoroacetyl, and
PROT' is hydrogen.

3. A compound according to claim 1, wherein PROT and PROT' together with the nitrogen atom to which they are attached form phthalimido-N-yl.

4. A compound according to claim 1, wherein PROT" is benzoyl or trityl.

5. A compound according to claim 1, wherein the compound is of formula

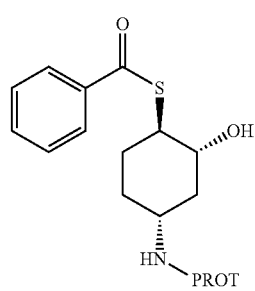

wherein PROT is selected from
ethoxycarbonyl,
2,2,2-trifluoroacetyl, and.

6. A compound according to claim 5, which is of formula

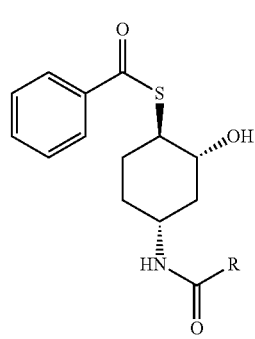

wherein R together with the C=O to which it is attached is ethoxycarbonyl or 2,2,2-trifluoroacetyl.

7. A compound according to claim 1, selected from the group consisting of:
{(1R, 2R, 4R)-4-[(2,2,2-Trifluoro-acetyl)-amino]-2-hydroxy-cyclohexyl}-benzene-carbothioate,
tert-Butyl [(1R, 3R, 4R)-3-hydroxy-4-tritylsulfanyl-cyclohexyl]-carbamate, and
2,2,2-Trifluoro-N-((1R, 3R, 4R)-3-hydroxy-4-tritylsulfanyl-cyclohexyl)-acetamide.

8. A compound according to claim 1, which is of formula

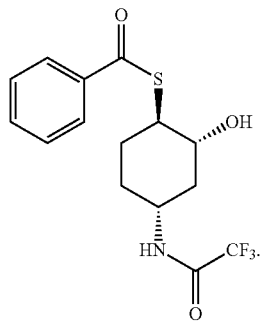

I$_{SSS}$

9. A process for the preparation of a compound of formula I according to claim 1, comprising
performing oxiran ring opening in a compound of formula

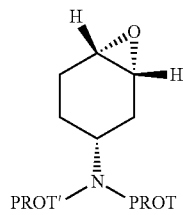

II or in a compound of formula

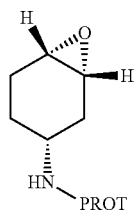

II$_S$ or in a compound of formula

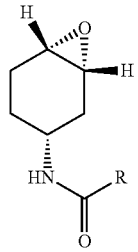

II$_{SS}$ or in a compound of formula

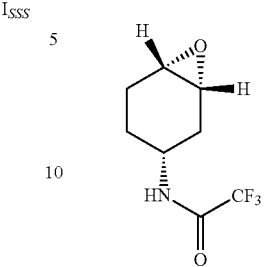

II$_{SSS}$ respectively, wherein PROT, PROT' and R are as defined in claim 1,
optionally by reaction with an optionally protected or activated thiol,
isolating a compound of formula I in the form of a single regioisomer and a single diastereomer from the reaction mixture;
wherein optionally a compound of formula II, II$_S$, II$_{SS}$ or II$_{SSS}$ is obtained by epoxidation of the double bond in a compound of formula

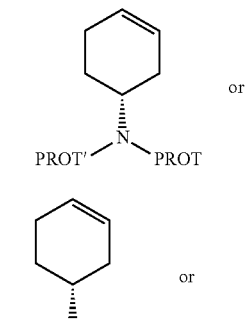

III

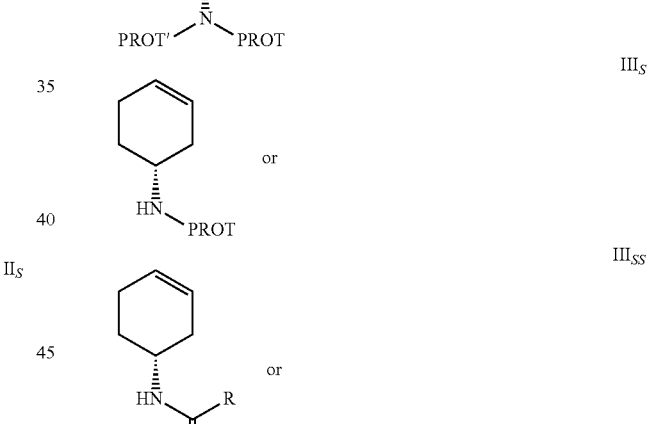

III$_S$

III$_{SS}$

III$_{SSS}$ and
isolating a compound formula II, II$_S$, II$_{SS}$ or II$_{SSS}$, wherein PROT, PROT' and R are as defined in claim 1, obtained from the reaction mixture.

10. A process according to claim 9 wherein formula II, IIs, IIss or IIsss is selected from the group consisting of
tert-Butyl (1R, 3R, 6R)-(7-oxa-bicyclo[4.1.0]hept-3-yl)-carbamate, and 2,2,2-Trifluoro-N-(1R, 3R, 6S)-(7-oxa-bicyclo[4.1.0]hept-3-yl)-acetamide.

11. A process for the production of a compound of formula I according to claim 1, wherein PROT' is hydrogen, comprising a) either reacting a compound of formula

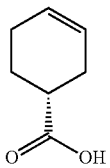

V with an azidoyl forming agent, optionally diphenylphosphoryl azide, optionally in the presence of a base, or reacting compound of formula V with an acid chloride forming agent, optionally oxalyl chloride or thionyl chloride, to obtain a compound of formula IX

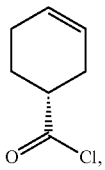

IX and further reacting a compound of formula IX with sodium azide, to obtain the acyl azide of formula

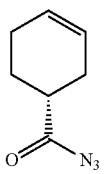

VI b) subjecting the acyl azide of formula VI to a Curtius rearrangement to obtain an isocyanate of formula

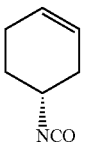

VII c) either reacting the isocyanate of step b) either via addition of an alcohol or via reaction with an strong organic acid and optionally in the presence of CuCl, or subjecting a compound of formula VII to hydrolysis with subsequent loss of carbon dioxide to obtain a compound of formula IV

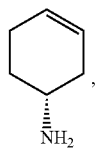

IV and further reacting a compound of formula IV with an amino protecting group, optionally in the presence of base, to obtain a compound of formula III, $III_S$, $III_{SS}$ or $III_{SSS}$, respectively,

III or

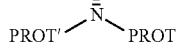

$III_S$

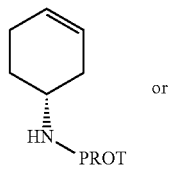

or $III_{SS}$

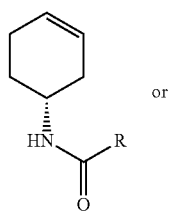

or $III_{SSS}$

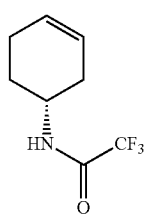

wherein PROT and R are as defined in claim 1 and PROT' is hydrogen, d) subjecting a compound of formula III, $III_S$, $III_{SS}$ or $III_{SSS}$, respectively, to epoxidation by use of an oxidation agent to obtain a corresponding oxiran of formula II, $II_S$, $II_{SS}$ or $II_{SSS}$, respectively,

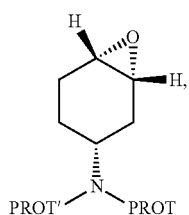

II

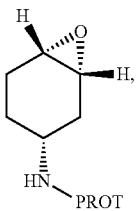  II$_S$

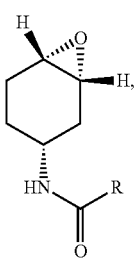  II$_{SS}$

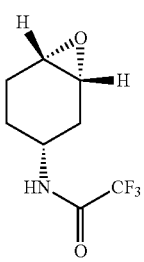  II$_{SSS}$ wherein PROT, PROT' and R are as defined in claim 1, and PROT' is hydrogen, in solution, e) subjecting a compound obtained in step d) to oxiran ring opening under introduction of a sulfur group in the side chain of the cyclohexyl ring via a sulfur donating agent, and f) directly isolating a compound of formula I according to claim 1, wherein PROT, PROT'' and R are as defined in claim 1, and PROT' is hydrogen,
   optionally by addition of an appropriate anti solvent,
   optionally whereby the reaction a) to e) is performed in a single solvent (system), and/or whereby none of the intermediates obtained in a) to d) is isolated, and
   isolating a compound of formula I in the form of a crystalline solid, from the reaction mixture.

12. A process according to claim 11, wherein none of the intermediates obtained in a) to d) is isolated.

13. A process according to claim 11, wherein the reaction a) to e) is performed in a single solvent (system).

14. A process for the preparation of a compound of formula I$_S$ according to claim 5, comprising
   performing oxiran ring opening in a compound of formula

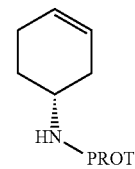  II$_S$ wherein PROT is an amine protective group,
optionally by reaction with an optionally protected or activated thiol, and isolating a compound of formula in the form of a single regioisomer and a single diastereomer from the reaction mixture;

wherein optionally the compound of formula II$_S$ is obtained by epoxidation of the double bond in a compound of formula

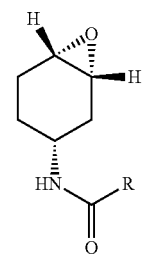  III$_S$ wherein PROT is an amine protecting group, and
isolating a compound formula II$_S$ obtained from the reaction mixture.

15. A process for the preparation of a compound of formula I$_{SS}$ according to claim 6, comprising
   performing oxiran ring opening in a compound of formula

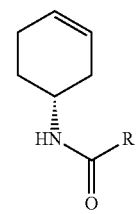  II$_{SS}$ wherein R is as defined in claim 6, optionally by reaction with an optionally protected or activated thiol, and isolating a compound of formula I$_{SS}$ in the form of a single regioisomer and a single diastereomer from the reaction mixture;

wherein optionally the compound of formula II$_{SS}$ is obtained by epoxidation of the double bond in a compound of formula

III$_{SS}$ wherein R is as defined in claim 6, and
isolating a compound formula II$_{SS}$ obtained from the reaction mixture.

16. A process for the preparation of a compound of formula I$_{SSS}$ according to claim 8, comprising performing oxiran ring opening in a compound of formula II$_{SSS}$

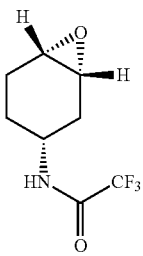

optionally by reaction with an optionally protected or activated thiol, and isolating a compound of formula I$_{SSS}$ in the form of a single regioisomer and a single diastereomer from the reaction mixture;

wherein optionally the compound of formula II$_{SSS}$ is obtained by epoxidation of the double bond in a compound of formula III$_{SSS}$

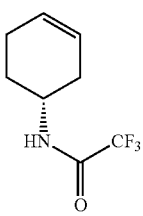

and isolating a compound formula II$_{SSS}$ obtained from the reaction mixture.

17. A process for the production of a compound of formula I$_S$ according to claim 5, comprising a) either reacting a compound of formula V

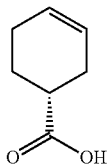

with an azidoyl forming agent, optionally diphenylphosphoryl azide, optionally in the presence of a base, or reacting compound of formula V with an acid chloride forming agent, optionally oxalyl chloride or thionyl chloride, to obtain a compound of formula IX

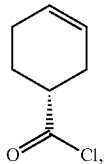

and further reacting a compound of formula IX with sodium azide, to obtain the acyl azide of formula VI

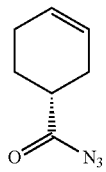

b) subjecting the acyl azide of formula VI to a Curtius rearrangement to obtain an isocyanate of formula VII

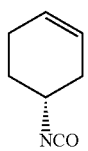

c) either reacting the isocyanate of step b) either via addition of an alcohol or via reaction with an strong organic acid and optionally in the presence of CuCl, or subjecting a compound of formula VII to hydrolysis with subsequent loss of carbon dioxide to obtain a compound of formula IV

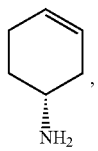

and further reacting a compound of formula IV with an amino protecting group, optionally in the presence of base, to obtain a compound of formula III$_S$,

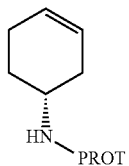

wherein PROT is an amine protective group, d) subjecting a compound of formula III$_S$ to epoxidation by use of an oxidation agent to obtain a corresponding oxiran of formula II$_S$

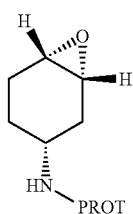

wherein PROT is an amine protective group, in solution, e) subjecting a compound obtained in step d) to oxiran ring opening under introduction of a sulfur group in the side chain of the cyclohexyl ring via a sulfur donating agent, and f) directly isolating a compound of formula I$_S$ according to claim 5, optionally by addition of an appropriate anti solvent, optionally whereby the reaction a) to e) is performed in a single solvent (system), and/or whereby none of the intermediates obtained in a) to d) is isolated, and isolating a compound of formula $I_S$ in the form of a crystalline solid, from the reaction mixture.

18. A process for the production of a compound of formula $I_{SS}$ according to claim 6, comprising a) either reacting a compound of formula

V

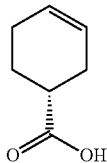

with an azidoyl forming agent, optionally diphenylphosphoryl azide, optionally in the presence of a base, or reacting compound of formula V with an acid chloride forming agent, optionally oxalyl chloride or thionyl chloride, to obtain a compound of formula IX

IX

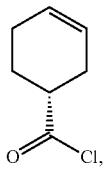

and further reacting a compound of formula IX with sodium azide, to obtain the acyl azide of formula

VI

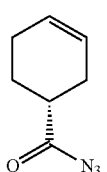

b) subjecting the acyl azide of formula VI to a Curtius rearrangement to obtain an isocyanate of formula

VII

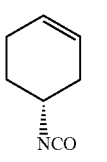

c) either reacting the isocyanate of step b) either via addition of an alcohol or via reaction with an strong organic acid and optionally in the presence of CuCl, or subjecting a compound of formula VII to hydrolysis with subsequent loss of carbon dioxide to obtain a compound of formula IV

IV

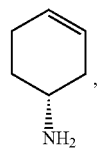

and further reacting a compound of formula IV with an amino protecting group, optionally in the presence of base, to obtain a compound of formula $III_{SS}$, $III_{SS}$

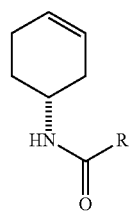

wherein R is as defined in claim 6, d) subjecting a compound of formula $III_{SS}$ to epoxidation by use of an oxidation agent to obtain a corresponding oxiran of formula $II_{SS}$ $II_{SS}$

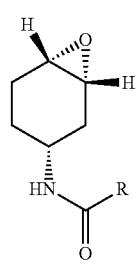

wherein R is as defined in claim 6, in solution, e) subjecting a compound obtained in step d) to oxiran ring opening under introduction of a sulfur group in the side chain of the cyclohexyl ring via a sulfur donating agent, and f) directly isolating a compound of formula $I_{SS}$ according to claim 6, optionally by addition of an appropriate anti solvent, optionally whereby the reaction a) to e) is performed in a single solvent (system), and/or whereby none of the intermediates obtained in a) to d) is isolated, and isolating a compound of formula $I_{SS}$ in the form of a crystalline solid, from the reaction mixture.

19. A process for the production of a compound of formula $I_{SSS}$ according to claim 8, comprising a) either reacting a compound of formula

V

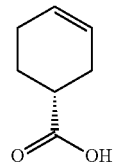

with an azidoyl forming agent, optionally diphenylphosphoryl azide, optionally in the presence of a base, or reacting compound of formula V with an acid chloride forming agent, optionally oxalyl chloride or thionyl chloride, to obtain a compound of formula IX

IX

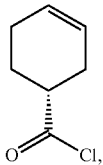

and further reacting a compound of formula IX with sodium azide, to obtain the acyl azide of formula

VI

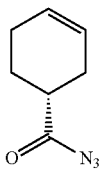

b) subjecting the acyl azide of formula VI to a Curtius rearrangement to obtain an isocyanate of formula

VII

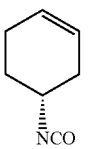

c) either reacting the isocyanate of step b) either via addition of an alcohol or via reaction with an strong organic acid and optionally in the presence of CuCl, or subjecting a compound of formula VII to hydrolysis with subsequent loss of carbon dioxide to obtain a compound of formula IV

IV

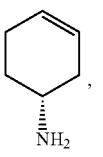

and further reacting a compound of formula IV with an amino protecting group, optionally in the presence of base, to obtain a compound of formula $III_{SSS}$, $III_{SSS}$

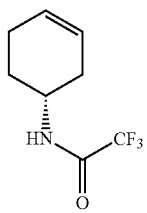

d) subjecting a compound of formula $III_{SSS}$ to epoxidation by use of an oxidation agent to obtain a corresponding oxiran of formula $II_{SSS}$ $II_{SSS}$

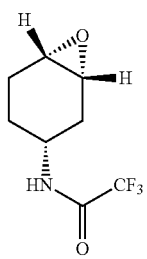

e) subjecting a compound obtained in step d) to oxiran ring opening under introduction of a sulfur group in the side chain of the cyclohexyl ring via a sulfur donating agent, and f) directly isolating a compound of formula $I_{SSS}$ according to claim 8, optionally by addition of an appropriate anti solvent, optionally whereby the reaction a) to e) is performed in a single solvent (system), and/or whereby none of the intermediates obtained in a) to d) is isolated, and isolating a compound of formula $I_{SSS}$ in the form of a crystalline solid, from the reaction mixture.

* * * * *

UNITED STATES PATENT AND TRADEMARK OFFICE
CERTIFICATE OF CORRECTION

Page 1 of 1

PATENT NO. : 8,987,498 B2
APPLICATION NO. : 13/699585
DATED : March 24, 2015
INVENTOR(S) : Riedl et al.

It is certified that error appears in the above-identified patent and that said Letters Patent is hereby corrected as shown below:

Specification

Column 5
Line 46, change "appropriate, e.g. according, e.g. analogously" to --appropriate, e.g. analogously--

Column 10
Line 64, change "III, $III_s$ or $III_{ss}$" to --III, $III_s$, $III_{ss}$ or $III_{sss}$--

Column 13
Line 24, "III, $III_s$ or $III_{ss}$" to --III, $III_s$, $III_{ss}$ or $III_{sss}$--

Column 19
Line 32, change "chloride wee added" to --chloride were added--

Signed and Sealed this
Fifth Day of April, 2016

Michelle K. Lee
*Director of the United States Patent and Trademark Office*